United States Patent
Hinkkanen

(10) Patent No.: US 6,770,460 B1
(45) Date of Patent: Aug. 3, 2004

(54) FUSION PROTEIN AND ITS USE IN AN IMMUNOASSAY FOR THE SIMULTANEOUS DETECTION OF AUTOANTIBODIES RELATED TO INSULIN-DEPENDENT DIABETES MELLITUS

(75) Inventor: Ari Hinkkanen, Turku (FI)

(73) Assignee: Wallac Oy, Turku (FI)

( * ) Notice: Subject to any disclaimer, the term of this patent is extended or adjusted under 35 U.S.C. 154(b) by 130 days.

(21) Appl. No.: 09/015,399

(22) Filed: Jan. 29, 1998

(51) Int. Cl.[7] .................................................. C12P 21/04
(52) U.S. Cl. ...................... 435/69.7; 435/7.1; 435/7.5; 435/320.1; 435/252.3; 435/252.33; 424/185.1; 424/193.1; 424/198.1; 530/403; 530/402; 530/412; 530/413; 530/303; 530/350; 536/23.4
(58) Field of Search .......................... 424/185.1, 193.1, 424/198.1; 435/7.1, 7.5, 320.1, 252.3, 252.33; 530/403, 402, 412, 413, 350; 536/23.4

(56) References Cited

U.S. PATENT DOCUMENTS 5,200,318 A * 4/1993 Rabin et al.
5,316,909 A * 5/1994 Xu
5,547,669 A * 8/1996 Rogers et al.
5,637,509 A * 6/1997 Hemmila et al.
5,989,551 A * 11/1999 Maclaren et al. ........ 424/185.1

FOREIGN PATENT DOCUMENTS

WO    WO 94/07464    * 3/1999

OTHER PUBLICATIONS

Hummel et al. J. Autoimmunity 9: 427, 1996.*
Borg et al. Clinical Chem. 43: 2358, 1997.*
Verge et al. J. Autoimmunity 9: 379, 1996.*
Berg et al. J. Imm. Methods 164: 221, 1993.*
Wiest–Ladenberg Diabetes 46: 568, 1992.*

* cited by examiner

*Primary Examiner*—G. R. Ewoldt
(74) *Attorney, Agent, or Firm*—Rothwell, Figg, Ernst & Manbeck, P.C.

(57) ABSTRACT

The invention relates to a fusion protein having epitopes of at least two of the autoantigens glutamic acid decarboxylase (GAD65), islet cell antigen (IA2) and preproinsulin (PPINS) wherenin said epitopes are connected with a linker peptide. The fusion protein must be able to bind to a solid phase.

The invention also concerns the cDNA, and a vector and cell comprising said cDNA. Furthermore, this invention relates to the use of said fusion protein in an immunoassay for the simultaneous detection of autoantibodies related to insulin-dependent diabetes mellitus.

16 Claims, 12 Drawing Sheets

| Flag-peptide | GAD65 | Not I | IA2 | Not I | PPINS | poly-his |
|---|---|---|---|---|---|---|
| DYKDDDDK- | ----------- | -KKKRPRKKK- | ----------- | -KKKRPRKKK- | ---------- | -CNGSHHHHHH |

FIG. 1a

| Flag-peptide | GAD65 | Sgf I | IA2 | Sgf I | PPINS | poly-his |
|---|---|---|---|---|---|---|
| DYKDDDDK- | ----------- | -KKKRSRKKK- | ----------- | -KKKRSRKKK- | ---------- | -CNGSHHHHHH |

FIG. 1b

MRRPRRPGGLGGSGGLRLLCLLLLSSRPGGCSAVSAHGCLFDRRLCSHLEVCIQDGLFGQCQVGVGQARPLLQVTSPVLQRL
QGVLRQLMSQGLSWHDDLTQYVISQEMERIPRLRPPEPRPRDRSGLAPKRPGPAGELLLQDIPTGSAPAAQHRLPQPPVGKGG
AGASSSLSPLQAELLPPLLEHLLPPQPPHPSLSYEPALLQPYLFHQFGSRDGSRVSEGSPGMVSVGPLPKAEAPALFSRTASKGI
FGDHPGHSYGDLPGPSPAQLFQDSGLLYLAQELPAPSRARVPRLPEQGSSSRAEDSPEGYEKEGLGDRGEKPASPAVQPDAAL
QRLAAVLAGYGVELRQLTPEQLSTLTLQLLPKGAGRNPGGVVNVGADIKKTMEGPVEGRDTAELPARTSPMPGHPTASPT
SSEVQQVPSPVSSEPPKAARPPVTPVLLEKKSPLGQSQPTVAGQPSARPAAEEYGYIVTDQKPLSLAAGVKLLEILAEHVHMSS
GSFINISVVGPALTFRIRHNEQNLSLADVTQQAGLVKSELEAQTGLQILQTGVGQREEAAAVLPQTAHSTSPMRSVLLTLVALA
GVAGLLVALAVALCVRQHARQQDKERLAALGPEGAHGDTTFEYQDLCRQHMATKSLFNRAEGPPEPSRVSSVSSQFSDAAQ
ASPSSHSSTPSWCEEPAQANMDISTGHMILAYMEDHLRNRDRLAKEWQALCAYQAEPNTCATAQEGNIKNRHPDFLPYDH
ARIKLKVESSPSRSDYINASPIEHDPRMPAYIATQGPLSHTIADFWQMVWESGCTVIVMLTPLVEDGVKQCDRYWPDEGASLY
HVYEVNLVSEHIWCEDFLVRSFYLKNVQTQETRTLTQFHFLSWPAEGTPASTRPLLDFRRKVNKCYRGRSCPIVHCSDGAGR
IGTYILIDMVLNRMAKGVKEIDIAATLEHVRDORPGLVRSKDQFEFALTAVAEEVNAILKALPQ

FIG. 2a

MASPGSGFWSFGSEDGSGDSENPGTARAWCQVAQKFTGGIGNKLCALLYGDAEKPAESGGSQPPRAAARKAACACDQKPCS
CSKVDVNYAFLHATDLLPACDGERPTLAFLQDVMNILLQYVVKSFDRSTKVIDFHYPNELLQEYNWELADOPQNLEEILMHC
QTTLKYAIKTGHPRYFNQLSTGLDMVGLAADWLTSTANTNMFTYEIAPVFVLLEYVTLKKMREIIGWPGGSGDGIFSPGGAIS
NMYAMMIARFKMFPEVKEKGMAALPRLIAFTSEHSHFSLKKGAAALGIGTDSVILIKCDERGKMIPSDLERRILEAKOKGFVPF
LVSATAGTTVYGAFDPLLAVADICKKYYKIWMHVDAAWGGGLLMSRKHKWKLSGVERANSVTWNPHKMMGVPLOCSALLV
REEGLMQNCNQMHASYLFQQDKHYDLSYDTGDKALOCGRHVDVFKLWLMWRAKGTTGFEAHVDKCLELAEYLYNIIKNR
EGYEMVFDGKPQHTNVCFWYIPPSLRTLEDNEERMSRLSKVAPVIKARMMEYGTTMVSYOPLGPKVNFFRMVISNPAATHQ
DIDFLFEIERLGQDL

FIG. 2b

MALWMRLLPLLALLALWGPDPAAAFVNQHLCGSHLVEALYLVCGERGFFYT
PKTRREAEDLQVGQVELGGGPGAGSLQPLALEGSLQKRGIVEQCCTSICSLYQ
LENYCN

FIG. 2c

```
   1 ACCCGCCCTC GCCGCTCGGC CCCGCGCGTC CCCGCGCGTG CCCTCCTCCC
  51 GCCACACGGC ACGCACGCGC GCGCAGGGCC AAGCCGAGGC AGCCGCCCGC
 101 AGCTCGCACT CGCTGGCGAC CTGCTCCAGT CTCCAAAGCC GATGGCATCT
 151 CCGGGCTCTG GCTTTTGGTC TTTCGGGTCG GAAGATGGCT CTGGGGATTC
 201 CGAGAATCCC GGCACAGCGC GAGCCTGGTG CCAAGTGGCT CAGAAGTTCA
 251 CGGGCGGCAT CGGAAACAAA CTGTGCGCCC TGCTCTACGG AGACGCCGAG
 301 AAGCCGGCGG AGAGCGGCGG GAGCCAACCC CCGCGGGCCG CCGCCCGGAA
 351 GGCCGCCTGC GCCTGCGACC AGAAGCCCTG CAGCTGCTCC AAAGTGGATG
 401 TCAACTACGC GTTTCTCCAT GCAACAGACC TGCTGCCGGC GTGTGATGGA

451 GAAAGGCCCA CTTTGGCGTT TCTGCAAGAT GTTATGAACA TTTTACTTCA
 501 GTATGTGGTG AAAAGTTTCG ATAGATCAAC CAAAGTGATT GATTTCCATT
 551 ATCCTAATGA GCTTCTCCAA GAATATAATT GGGAATTGGC AGACCAACCA
 601 CAAAATTTGG AGGAAATTTT GATGCATTGC CAAACAACTC TAAAATATGC
 651 AATTAAAACA GGGCATCCTA GATACTTCAA TCAACTTTCT ACTGGTTTGG
 701 ATATGGTTGG ATTAGCAGCA GACTGGCTGA CATCAACAGC AAATACTAAC
 751 ATGTTCACCT ATGAAATTGC TCCAGTATTT GTGCTTTTGG AATATGTCAC
 801 ACTAAAGAAA ATGAGAGAAA TCATTGGCTG GCCAGGGGGC TCTGGCGATG
 851 GGATATTTTC TCCCGGTGGC GCCATATCTA ACATGTATGC CATGATGATC
 901 GCACGCTTTA AGATGTTCCC AGAAGTCAAG GAGAAAGGAA TGGCTGCTCT
 951 TCCCAGGCTC ATTGCCTTCA CGTCTGAACA TAGTCATTTT TCTCTCAAGA
1001 AGGGAGCTGC AGCCTTAGGG ATTGGAACAG ACAGCGTGAT TCTGATTAAA
1051 TGTGATGAGA GAGGGAAAAT GATTCCATCT GATCTTGAAA GAAGGATTCT
1101 TGAAGCCAAA CAGAAAGGGT TTGTTCCTTT CCTCGTGAGT GCCACAGCTG
1151 GAACCACCGT GTACGGAGCA TTTGACCCCC TCTTAGCTGT CGCTGACATT
1201 TGCAAAAAGT ATAAGATCTG GATGCATGTG GATGCAGCTT GGGGTGGGGG
1251 ATTACTGATG TCCCGAAAAC ACAAGTGGAA ACTGAGTGGC GTGGAGAGGG
```

FIG. 3a

```
1301 CCAACTCTGT GACGTGGAAT CCACACAAGA TGATGGGAGT CCCTTTGCAG

1351 TGCTCTGCTC TCCTGGTTAG AGAAGAGGGA TTGATGCAGA ATTGCAACCA

1401 AATGCATGCC TCCTACCTCT TTCAGCAAGA TAAACATTAT GACCTGTCCT

1451 ATGACACTGG AGACAAGGCC TTACAGTGCG GACGCCACGT TGATGTTTTT

1501 AAACTATGGC TGATGTGGAG GGCAAAGGGG ACTACCGGGT TTGAAGCGCA

1551 TGTTGATAAA TGTTTGGAGT TGGCAGAGTA TTTATACAAC ATCATAAAAA

1601 ACCGAGAAGG ATATGAGATG GTGTTTGATG GGAAGCCTCA GCACACAAAT

1651 GTCTGCTTCT GGTACATTCC TCCAAGCTTG CGTACTCTGG AAGACAATGA

1701 AGAGAGAATG AGTCGCCTCT CGAAGGTGGC TCCAGTGATT AAAGCCAGAA

1751 TGATGGAGTA TGGAACCACA ATGGTCAGCT ACCAACCCTT GGGAGACAAG

1801 GTCAATTTCT TCCGCATGGT CATCTCAAAC CCAGCGGCAA CTCACCAAGA

1851 CATTGACTTC CTGATTGAAG AAATAGAACG CCTTGGACAA GATTTATAAT

1901 AACCTTGCTC ACCAAGCTGT TCCACTTCTC TAGAGAACAT GCCCTCAGCT

1951 AAGCCCCCTA CTGAGAAACT TCCTTTGAGA ATTGTGCGAC TTCACAAAAT

2001 GCAAGGTGAA CACCACTTTG TCTCTGAGAA CAGACGTTAC CAATTATGGA

2051 GTGTCACCAG CTGCCAAAAT CGTAGGTGTT GGCTCTGCTG GTCACTGGAG

2101 TAGTTGCTAC TCTTCAGAAT ATGGACAAAG AAGGCACAGG TGTAAATATA

2151 GTAGCAGGAT GAGGAACCTC AAACTGGGTA TCATTTGCAC GTGCTCTTCT

2201 GTTCTCAAAT GCTAAATGCA AACACTGTGT ATTTATTAGT TAGGTGTGCC

2251 AAACTACCGT TCCCAAATTG GTGTTTCTGA ATGACATCAA CATTCCCCCA

2301 ACATTACTCC ATTACTAAAG ACAGAAAAAA ATAAAAACAT AAAATATACA

2351 AACATGTGGC AACCTGTTCT TCCTACCAAA TATAAACTTG TGTATGATCC

2401 AAGTATTTTA TCTGTGTTGT CTCTCTAAAC CCAAATAAAT GTGTAAATGT

2451 GGACACA
```

FIG. 3b

```
   1 CAGCCCCTCT GGCAGGCTCC CGCCAGCGTC GCTGCGGCTC CGGCCCGGGA
  51 GCGAGCGCCC GGAGCTCGGA AAGATGCGGC GCCCGCGGCG GCCTGGGGGT
 101 CTCGGGGGAT CCGGGGGTCT CCGGCTGCTC CTCTGCCTCC TGCTGCTGAG
 151 CAGCCGCCCG GGGGGCTGCA GCGCCGTTAG TGCCCACGGC TGTCTATTTG
 201 ACCGCAGGCT CTGCTCTCAC CTGGAAGTCT GTATTCAGGA TGGCTTGTTT
 251 GGGCAGTGCC AGGTGGGAGT GGGGCAGGCC CGGCCCCTTT GCAAGTCAC
 301 CTCCCCAGTT CTCCAACGCT ACAAGGTGT GCTCCGACAA CTCATGTCCC
 351 AAGGATTGTC CTGGCACGAT GACCTCACCC AGTATGTGAT CTCTCAGGAG
 401 ATGGAGCGCA TCCCCAGGCT TCGCCCCCCA GAGCCCCGTC CAAGGGACAG
 451 GTCTGGCTTG GCACCCAAGA GACCTGGTCC TGCTGGAGAG CTGCTTTTAC
 501 AGGACATCCC CACTGGCTCC GCCCCTGCTG CCCAGCATCG GCTTCCACAA
 551 CCACCAGTGG GCAAAGGTGG AGCTGGGGCC AGCTCCTCTC TGTCCCCTCT
 601 GCAGGCTGAG CTGCTCCCGC CTCTCTTGGA GCACCTGCTG CTGCCCCCAC
 651 AGCCTCCCCA CCCTTCACTG AGTTACGAAC CTGCCTTGCT GCAGCCCTAC
 701 CTGTTCCACC AGTTTGGCTC CCGTGATGGC TCCAGGGTCT CAGAGGGCTC
 751 CCCAGGGATG GTCAGTGTCG GCCCCCTGCC CAAGGCTGAA GCCCCTGCCC
 801 TCTTCAGCAG AACTGCCTCC AAGGGCATAT TTGGGGACCA CCCTGGCCAC
 851 TCCTACGGGG ACCTTCCAGG GCCTTCACCT GCCCAGCTTT TTCAAGACTC
 901 TGGGCTGCTC TATCTGGCCC AGGAGTTGCC AGCACCCAGC AGGGCCAGGG
 951 TGCCAAGGCT GCCAGAGCAA GGGAGCAGCA GCCGGGCAGA GGACTCCCCA
1001 GAGGGCTATG AGAAGGAAGG ACTAGGGGAT CGTGGAGAGA AGCCTGCTTC
1051 CCCAGCTGTG CAGCCAGATG CGGCTCTGCA GAGGCTGGCC GCTGTGCTGG
1101 CGGGCTATGG GGTAGAGCTG CGTCAGCTGA CCCCTGAGCA GCTCTCCACA
1151 CTCCTGACCC TGCTGCAGCT ACTGCCCAAG GGTGCAGGAA GAAATCCGGG
1201 AGGGGTTGTA AATGTTGGAG CTGATATCAA GAAAACAATG GAGGGGCCGG
1251 TGGAGGGCAG AGACACAGCA GAGCTTCCAG CCCGCACATC CCCCATGCCT
```

FIG. 3c

1301 GGACACCCCA CTGCCAGCCC TACCTCCAGT GAAGTCCAGC AGGTGCCAAG

1351 CCCTGTCTCC TCTGAGCCTC CCAAAGCTGC CAGACCCCCT GTGACACCTG

1401 TCCTGCTAGA GAAGAAAAGC CCACTGGGCC AGAGCCAGCC CACGGTGGCA

1451 GGACAGCCCT CAGCCCGCCC AGCAGCAGAG GAATATGGCT ACATCGTCAC

1501 TGATCAGAAG CCCCTGAGCC TGGCTGCAGG AGTGAAGCTG CTGGAGATCC

1551 TGGCTGAGCA TGTGCACATG TCCTCAGGCA GCTTCATCAA CATCAGTGTG

1601 GTGGGACCAG CCCTCACCTT CCGCATCCGG CACAATGAGC AGAACCTGTC

1651 TTTGGCTGAT GTGACCCAAC AAGCAGGGCT GGTGAAGTCT GAACTGGAAG

1701 CACAGACAGG GCTCCAAATC TTGCAGACAG GAGTGGGACA GAGGGAGGAG

1751 GCAGCTGCAG TCCTTCCCCA AACTGCGCAC AGCACCTCAC CCATGCGCTC

1801 AGTGCTGCTC ACTCTGGTGG CCCTGGCAGG TGTGGCTGGG CTGCTGGTGG

1851 CTCTGGCTGT GGCTCTGTGT GTGCGGCAGC ATGCGCGGCA GCAAGACAAG

1901 GAGCGCCTGG CAGCCCTGGG GCCTGAGGGG GCCCATGGTG ACACTACCTT

1951 TGAGTACCAG GACCTGTGCC GCCAGCACAT GGCCACGAAG TCCTTGTTCA

2001 ACCGGGCAGA GGGTCCACCG GAGCCTTCAC GGGTGAGCAG TGTGTCCTCC

2051 CAGTTCAGCG ACGCAGCCCA GGCCAGCCCC AGCTCCCACA GCAGCACCCC

2101 GTCCTGGTGC GAGGAGCCGG CCCAAGCCAA CATGGACATC TCCACGGGAC

2151 ACATGATTCT GGCATACATG GAGGATCACC TGCGGAACCG GGACCGCCTT

2201 GCCAAGGAGT GGCAGGCCCT CTGTGCCTAC CAAGCAGAGC CAAACACCTG

2251 TGCCACCGCG CAGGGGGAGG GCAACATCAA AAAGAACCGG CATCCTGACT

2301 TCCTGCCCTA TGACCATGCC CGCATAAAAC TGAAGGTGGA GAGCAGCCCT

2351 TCTCGGAGCG ATTACATCAA CGCCAGCCCC ATTATTGAGC ATGACCCTCG

2401 GATGCCAGCC TACATAGCCA CGCAGGGCCC GCTGTCCCAT ACCATCGCAG

2451 ACTTCTGGCA GATGGTGTGG GAGAGCGGCT GCACCGTCAT CGTCATGCTG

2501 ACCCCGCTGG TGGAGGATGG TGTCAAGCAG TGTGACCGCT ACTGGCCAGA

2551 TGAGGGTGCC TCCCTCTACC ACGTATATGA GGTGAACCTG GTGTCGGAGC

2601 ACATCTGGTG CGAGGACTTT CTGGTGCGGA GCTTCTACCT GAAGAACGTG

2651 CAGACCCAGG AGACGCGCAC GCTCACGCAG TTCCACTTCC TCAGCTGGCC

FIG. 3d

2701 GGCAGAGGGC ACACCGGCCT CCACGCGGCC CCTGCTGGAC TTCCGCAGGA

2751 AGGTGAACAA GTGCTACCGG GGCCGCTCCT GCCCCATCAT CGTGCACTGC

2801 AGTGATGGTG CGGGGAGGAC CGGCACCTAC ATCCTCATCG ACATGGTCCT

2851 GAACCGCATG GCAAAAGGAG TGAAGGAGAT TGACATCGCT GCCACCCTGG

2901 AGCATGTCCG TGACCAGCGG CCTGGCCTTG TCCGCTCTAA GGACCAGTTT

2951 GAATTTGCCC TGACAGCCGT GGCGGAGGAA GTGAATGCCA TCCTCAAGGC

3001 CCTGCCCCAG TGAGACCCTG GGGCCCCTTG GCGGGCAGCC CAGCCTCTGT

3051 CCCTCTTTGC CTGTGTGAGC ATCTCTGTGT ACCCACTCCT CACTGCCCCA

3101 CCAGCCACCT CTTGGGCATG CTCAGCCCTT CCTAGAAGAG TCAGGAAGGG

3151 AAAGCCAGAA GGGGCACGCC TGCCCAGCCT CGCATGCCAG AGCCTGGGGC

3201 ATCCCAGAGC CCAGGGCATC CCATGGGGGT GCTGCAGCCA GGAGGAGAGG

3251 AAAGGACATG GGTAGCAATT CTACCCAGAG CCTTCTCCTG CCTACATTCC

3301 CTGGCCTGGC TCTCCTGTAG CTCTCCTGGG GTTCTGGGAG TTCCCTGAAC

3351 ATCTGTGTGT GTCCCCCTAT GCTCCAGTAT GGAAGAATGG GGTGGAGGGT

3401 CGCCACACCC GGCTCCCCCT GCTTCTCAGC CCCGGGCCTG CCTCTGACTC

3451 ACACTTGGGC GCTCTGCCCT CCCTGGCCTC ACGCCCAGCC TGGTCCCACC

3501 ACCCTCCCAC CATGCGCTGC TCAACCTCTC TCCTTCTGGC GCAAGAGAAC

3551 ATTTCTAGAA AAAACTACTT TTGTACCAGT GTGAATAAAG TTAGTGTGTT

3601 GTCTGTGCAG CTG

FIG. 3e

```
   1 CTCGAGGGGC CTAGACATTG CCCTCCAGAG AGAGCACCCA ACACCCTCCA
  51 GGCTTGACCG GCCAGGGTGT CCCCTTCCTA CCTTGGAGAG AGCAGCCCCA
 101 GGGCATCCTG CAGGGGGTGC TGGGACACCA GCTGGCCTTC AAGGTCTCTG
 151 CCTCCCTCCA GCCACCCCAC TACACGCTGC TGGGATCCTG GATCTCAGCT
 201 CCCTGGCCGA CAACACTGGC AAACTCCTAC TCATCCACGA AGGCCCTCCT
 251 GGGCATGGTG GTCCTTCCCA GCCTGGCAGT CTGTTCCTCA CACACCTTGT
 301 TAGTGCCCAG CCCCTGAGGT TGCAGCTGGG GGTGTCTCTG AAGGGCTGTG
 351 AGCCCCCAGG AAGCCCTGGG GAAGTGCCTG CCTTGCCTCC CCCCGGCCCT
 401 GCCAGCGCCT GGCTCTGCCC TCCTACCTGG GCTCCCCCCA TCCAGCCTCC
 451 CTCCCTACAC ACTCCTCTCA AGGAGGCACC CATGTCCTCT CCAGCTGCCG
 501 GGCCTCAGAG CACTGTGGCG TCCTGGGGCA GCCACCGCAT GTCCTGCTGT
 551 GGCATGGCTC AGGGTGGAAA GGGCGGAAGG GAGGGGTCCT GCAGATAGCT
 601 GGTGCCCACT ACCAAACCCG CTCGGGGCAG GAGAGCCAAA GGCTGGGTGT
 651 GTGCAGAGCG GCCCCGAGAG GTTCCGAGGC TGAGGCCAGG GTGGGACATA
 701 GGGATGCGAG GGGCCGGGGC ACAGGATACT CCAACCTGCC TGCCCCCATG
 751 GTCTCATCCT CCTGCTTCTG GGACCTCCTG ATCCTGCCCC TGGTGCTAAG
 801 AGGCAGGTAA GGGGCTGCAG GCAGCAGGGC TCGGAGCCCA TGCCCCCTCA
 851 CCATGGGTCA GGCTGGACCT CCAGGTGCCT GTTCTGGGGA GCTGGGAGGG
 901 CCGGAGGGGT GTACCCCAGG GGCTCAGCCC AGATGACACT ATGGGGGTGA
 951 TGGTGTCATG GGACCTGGCC AGGAGAGGGG AGATGGGCTC CAGAAGAGG
1001 AGTGGGGGCT GAGAGGGTGC CTGGGGGGCC AGGACGGAGC TGGGCCAGTG
1051 CACAGCTTCC CACACCTGCC CACCCCAGA GTCCTGCCGC CACCCCCAGA
1101 TCACACGGAA GATGAGGTCC GAGTGGCCTG CTGAGGACTT GCTGCTTGTC
1151 CCCAGGTCCC CAGGTCATGC CCTCCTTCTG CCACCCTGGG GAGCTGAGGG
1201 CCTCAGCTGG GGCTGCTGTC CTAAGGCAGG GTGGGAACTA GCAGCCAGC
1251 AGGGAGGGGA CCCCTCCCTC ACTCCCACTC TCCCACCCCC ACCACCTTGG
1301 CCCATCCATG GCGGCATCTT GGGCCATCCG GGACTGGGGA CAGGGGTCCT
1351 GGGGACAGGG GTCCGGGGAC AGGGTCCTGG GGACAGGGGT GTGGGGACAG
```

FIG. 3f

```
1401 GGGTCTGGGG ACAGGGGTGT GGGGACAGGG GTGTGGGGAC AGGGGTCTGG
1451 GGACAGGGGT GTGGGGACAG GGGTCCGGGG ACAGGGGTGT GGGGACAGGG
1501 GTCTGGGGAC AGGGGTGTGG GACAGGGGT GTGGGGACAG GGGTCTGGGG
1551 ACAGGGGTGT GGGGACAGGG GTCCTGGGGA CAGGGGTGTG GGGACAGGGG
1601 TGTGGGGACA GGGGTGTGGG GACAGGGGTG TGGGGACAGG GGTCCTGGGG
1651 ATAGGGGTGT GGGGACAGGG GTGTGGGGAC AGGGGTCCCG GGGACAGGGG
1701 TGTGGGGACA GGGGTGTGGG GACAGGGGTC CTGGGGACAG GGGTCTGAGG
1751 ACAGGGGTGT GGGCACAGGG GTCCTGGGGA CAGGGGTCCT GGGGACAGGG
1801 GTCCTGGGGA CAGGGGTCTG GGGACAGCAG CGCAAAGAGC CCCGCCCTGC
1851 AGCCTCCAGC TCTCCTGGTC TAATGTGGAA AGTGGCCCAG GTGAGGGCTT
1901 TGCTCTCCTG GAGACATTTG CCCCAGCTG TGAGCAGGGA CAGGTCTGGC
1951 CACCGGGCCC CTGGTTAAGA CTCTAATGAC CCGCTGGTCC TGAGGAAGAG
2001 GTGCTGACGA CCAAGGAGAT CTTCCCACAG ACCCAGCACC AGGGAAATGG
2051 TCCGGAAATT GCAGCCTCAG CCCCCAGCCA TCTGCCGACC CCCCCACCCC
2101 GCCCTAATGG GCCAGGCGGC AGGGGTTGAC AGGTAGGGGA GATGGGCTCT
2151 GAGACTATAA AGCCAGCGGG GGCCCAGCAG CCCTCAGCCC TCCAGGACAG
2201 GCTGCATCAG AAGAGGCCAT CAAGCAGGTC TGTTCCAAGG GCCTTTGCGT
2251 CAGGTGGGCT CAGGGTTCCA GGGTGGCTGG ACCCCAGGCC CCAGCTCTGC
2301 AGCAGGGAGG ACGTGGCTGG GCTCGTGAAG CATGTGGGGG TGAGCCCAGG
2351 GGCCCCAAGG CAGGGCACCT GGCCTTCAGC CTGCCTCAGC CTGCCTGTC
2401 TCCCAGATCA CTGTCCTTCT GCCATGGCCC TGTGGATGCG CCTCCTGCCC
2451 CTGCTGGCGC TGCTGGCCCT CTGGGGACCT GACCCAGCCG CAGCCTTTGT
2501 GAACCAACAC CTGTGCGGCT CACACCTGGT GGAAGCTCTC TACCTAGTGT
2551 GCGGGGAACG AGGCTTCTTC TACACACCCA AGACCCGCCG GGAGGCAGAG
2601 GACCTGCAGG GTGAGCCAAC CGCCCATTGC TGCCCCTGGC CGCCCCCAGC
2651 CACCCCCTGC TCCTGGCGCT CCCACCCAGC ATGGGCAGAA GGGGGCAGGA
2701 GGCTGCCACC CAGCAGGGGG TCAGGTGCAC TTTTTTAAAA AGAAGTTCTC
2751 TTGGTCACGT CCTAAAAGTG ACCAGCTCCC TGTGGCCCAG TCAGAATCTC
2801 AGCCTGAGGA CGGTGTTGGC TTCGGCAGCC CCGAGATACA TCAGAGGGTG
2851 GGCACGCTCC TCCCTCCACT CGCCCCTCAA ACAAATGCCC CGCAGCCCAT
```

FIG. 3g

2901 TTCTCCACCC TCATTTGATG ACCGCAGATT CAAGTGTTTT GTTAAGTAAA
2951 GTCCTGGGTG ACCTGGGGTC ACAGGGTGCC CCACGCTGCC TGCCTCTGGG
3001 CGAACACCCC ATCACGCCCG GAGGAGGGCG TGGCTGCCTG CCTGAGTGGG
3051 CCAGACCCCT GTCGCCAGCC TCACGGCAGC TCCATAGTCA GGAGATGGGG
3101 AAGATGCTGG GGACAGGCCC TGGGGAGAAG TACTGGGATC ACCTGTTCAG
3151 GCTCCCACTG TGACGCTGCC CCGGGGCGGG GGAAGGAGGT GGGACATGTG
3201 GGCGTTGGGG CCTGTAGGTC CACACCCAGT GTGGGTGACC CTCCCTCTAA
3251 CCTGGGTCCA GCCCGGCTGG AGATGGGTGG GAGTGCGACC TAGGGCTGGC
3301 GGGCAGGCGG GCACTGTGTC TCCCTGACTG TGTCCTCCTG TGTCCCTCTG
3351 CCTCGCCGCT GTTCCGGAAC CTGCTCTGCG CGGCACGTCC TGGCAG<u>TGGG</u>
3401 <u>GCAGGTGGAG CTGGGCGGGG GCCCTGGTGC AGGCAGCCTG CAGCCCTTGG</u>
3451 <u>CCCTGGAGGG GTCCCTGCAG AAGCGTGGCA TTGTGGAACA ATGCTGTACC</u>
3501 <u>AGCATCTGCT CCCTCTACCA GCTGGAGAAC TACTGCAAC</u>T AGACGCAGCC
3551 TGCAGGCAGC CCCACACCCG CCGCCTCCTG CACCGAGAGA GATGGAATAA
3601 AGCCCTTGAA CCAGCCCTGC TGTGCCGTCT GTGTGTCTTG GGGGCCCTGG
3651 GCCAAGCCCC ACTTCCCGGC ACTGTTGTGA GCCCCTCCCA GCTCTCTCCA
3701 CGCTCTCTGG GTGCCCACAG GTGCCAACGC CAGGCAGGCC CAGCATGCAG
3751 TGGCTCTCCC CAAAGCGGCC ATGCCTGTTG GCTGCCTGCT GCCCCCACCC
3801 TGTGGCTCAG GGTCCAGTAT GGGAGCTTCG GGGGTCTCTG AGGGGCCAGG
3851 GATGGTGGGG CCACTGAGAA GTGACTCTGT CAGTAGCCGA CCTGGAGTCC
3901 CCAGAGACCT TGTTCAGGAA AGGGAATGAG AACATTCCAG CAATTTTCCC
3951 CCCACCTAGC CCTCCCAGGT TCTATTTTTA GAGTTATTTC TGATGGAGTC
4001 CCTGTGGAGG GAGGAGGCTG GGCTGAGGGA GGGGGTCCTG CAGGGCGGGG
4051 GGCTGGGAAG GTGGGGAGAG CTGCCGAGA GCCACCCGCT ATCCCCAGCT
4101 CTGGGCAGCC CCGGGACAGT CACACACCCT GGCCTCGCGG CCCAAGCTGG
4151 CAGCCGTCTG CAGCCACAGC TTATGCCAGC CCAGGTCCAG CCAGACACCT
4201 GAGGGACCCA CTGGTGCCTT GGAGGAAGCA GGAGAGGTCA GATGGCACCA
4251 TGAGCTGGGG CAGGTGCAGG GACCGTGGCA GCACCTGGCA GGGCCTCAGA
4301 ACCCATGCCT TGGGCACCCC GGCCATGAGG CCCTGAGGAT TGCAGCCCAA
4351 GAGAAGCAGG GAACGCCAGG GCCACAGGGG CAGAGACCAG GCCAGGGTCC

FIG. 3h

```
4401 CTTGCGGCCC TTAGCCCACC CCCTCCCAGT AAGCAGGGGC TGCTTGGCTA
4451 GGCTTCCTTT TGCTACAGAC CTGCTGCTCA CCCAGAGGCC CACGGGCCCT
4501 AGTGACAAGG TCGTTGTGGC TCCAGGTCCT TGGGGGTCCT GACACAGAGC
4551 CTCTTCTGCA GCACCCCTGA GGACAGGGTG CTCCGCTGGG CACCCAGCCT
4601 AGTGGGCAGA CGAGAACCTA GGGGCTGCCT GGGCCTACTG TGGCCTGGGA
4651 GGTCAGCGGG TGACCCTAGC TACCCTGTGG CTGGGCCAGT CTGCCTGCCA
4701 CCCAGGCCAA ACCAATCTGC ACCTTTCCTG AGAGCTCCAC CCAGGGCTGG
4751 GCTGGGGATG GCTGGGCCTG GGCTGGCAT GGGCTGTGGC TGCAGACCAC
4801 TGCCAGCTTG GGCCTCGAGG CCAGGAGCTC ACCCTCCAGC TGCCCCGCCT
4851 CCAGAGTGGG GGCCAGGGCT GGGCAGGCGG GTGGACGGCC GGACACTGGC
4901 CCCGGAAGAG GAGGGAGGCG GTGGCTGGGA TCGGCAGCAG CCGTCCATGG
4951 GAACACCCAG CCGGCCCCAC TCGCACGGGT AGAGACAGGC GC
```

FIG. 3i

SEQUENCE LISTING (1) GENERAL INFORMATION:

(iii) NUMBER OF SEQUENCES: 13

(2) INFORMATION FOR SEQ ID NO:1:

(i) SEQUENCE CHARACTERISTICS:
      (A) LENGTH: 8 amino acids
      (B) TYPE: amino acid
      (C) STRANDEDNESS:
      (D) TOPOLOGY: linear (ii) MOLECULE TYPE: peptide (v) FRAGMENT TYPE: N-terminal (xi) SEQUENCE DESCRIPTION: SEQ ID NO:1:

Asp Tyr Lys Asp Asp Asp Asp Lys
1                 5

(2) INFORMATION FOR SEQ ID NO:2:

(i) SEQUENCE CHARACTERISTICS:
      (A) LENGTH: 9 amino acids
      (B) TYPE: amino acid
      (C) STRANDEDNESS:
      (D) TOPOLOGY: linear (ii) MOLECULE TYPE: peptide (v) FRAGMENT TYPE: internal (xi) SEQUENCE DESCRIPTION: SEQ ID NO:2:

Lys Lys Lys Arg Pro Arg Lys Lys Lys
1                 5

(2) INFORMATION FOR SEQ ID NO:3:

(i) SEQUENCE CHARACTERISTICS:
      (A) LENGTH: 10 amino acids
      (B) TYPE: amino acid

```
        (C) STRANDEDNESS:
        (D) TOPOLOGY: linear (ii) MOLECULE TYPE: peptide (v) FRAGMENT TYPE: C-terminal (xi) SEQUENCE DESCRIPTION: SEQ ID NO:3:

Cys Asn Gly Ser His His His His His
1               5                  10

(2) INFORMATION FOR SEQ ID NO:4:

(i) SEQUENCE CHARACTERISTICS:
         (A) LENGTH: 9 amino acids
         (B) TYPE: amino acid
         (C) STRANDEDNESS:
         (D) TOPOLOGY: linear (ii) MOLECULE TYPE: peptide (v) FRAGMENT TYPE: internal (xi) SEQUENCE DESCRIPTION: SEQ ID NO:4:

Lys Lys Lys Arg Ser Arg Lys Lys Lys
1               5

(2) INFORMATION FOR SEQ ID NO:5:

(i) SEQUENCE CHARACTERISTICS:
         (A) LENGTH: 979 amino acids
         (B) TYPE: amino acid
         (C) STRANDEDNESS:
         (D) TOPOLOGY: linear (ii) MOLECULE TYPE: protein (xi) SEQUENCE DESCRIPTION: SEQ ID NO:5:

Met Arg Arg Pro Arg Pro Gly Gly Leu Gly Gly Ser Gly Gly Leu
1               5                  10                  15

Arg Leu Leu Leu Cys Leu Leu Leu Ser Ser Arg Pro Gly Gly Cys
                20                  25                  30

Ser Ala Val Ser Ala His Gly Cys Leu Phe Asp Arg Arg Leu Cys Ser
                35                  40                  45

His Leu Glu Val Cys Ile Gln Asp Gly Leu Phe Gly Gln Cys Gln Val
    50                  55                  60

Gly Val Gly Gln Ala Arg Pro Leu Leu Gln Val Thr Ser Pro Val Leu
65                  70                  75                  80

Gln Arg Leu Gln Gly Val Leu Arg Gln Leu Met Ser Gln Gly Leu Ser
                85                  90                  95

Trp His Asp Asp Leu Thr Gln Tyr Val Ile Ser Gln Glu Met Glu Arg
                100                 105                 110

Ile Pro Arg Leu Arg Pro Pro Glu Pro Arg Pro Arg Asp Arg Ser Gly
                115                 120                 125

Leu Ala Pro Lys Arg Pro Gly Pro Ala Gly Glu Leu Leu Leu Gln Asp
                130                 135                 140

Ile Pro Thr Gly Ser Ala Pro Ala Ala Gln His Arg Leu Pro Gln Pro
145                 150                 155                 160

Pro Val Gly Lys Gly Gly Ala Gly Ala Ser Ser Ser Leu Ser Pro Leu
                165                 170                 175

Gln Ala Glu Leu Leu Pro Pro Leu Leu Glu His Leu Leu Leu Pro Pro
                180                 185                 190
```

-continued

```
Gln Pro Pro His Pro Ser Leu Ser Tyr Glu Pro Ala Leu Leu Gln Pro
            195                 200                 205
Tyr Leu Phe His Gln Phe Gly Ser Arg Asp Gly Ser Arg Val Ser Glu
        210                 215                 220
Gly Ser Pro Gly Met Val Ser Val Gly Pro Leu Pro Lys Ala Glu Ala
225                 230                 235                 240
Pro Ala Leu Phe Ser Arg Thr Ala Ser Lys Gly Ile Phe Gly Asp His
                245                 250                 255
Pro Gly His Ser Tyr Gly Asp Leu Pro Gly Pro Ser Pro Ala Gln Leu
            260                 265                 270
Phe Gln Asp Ser Gly Leu Leu Tyr Leu Ala Gln Glu Leu Pro Ala Pro
        275                 280                 285
Ser Arg Ala Arg Val Pro Arg Leu Pro Glu Gln Gly Ser Ser Ser Arg
290                 295                 300
Ala Glu Asp Ser Pro Glu Gly Tyr Glu Lys Glu Gly Leu Gly Asp Arg
305                 310                 315                 320
Gly Glu Lys Pro Ala Ser Pro Ala Val Gln Pro Asp Ala Ala Leu Gln
                325                 330                 335
Arg Leu Ala Ala Val Leu Ala Gly Tyr Gly Val Glu Leu Arg Gln Leu
            340                 345                 350
Thr Pro Glu Gln Leu Ser Thr Leu Leu Thr Leu Leu Gln Leu Leu Pro
        355                 360                 365
Lys Gly Ala Gly Arg Asn Pro Gly Gly Val Val Asn Val Gly Ala Asp
370                 375                 380
Ile Lys Lys Thr Met Glu Gly Pro Val Glu Gly Arg Asp Thr Ala Glu
385                 390                 395                 400
Leu Pro Ala Arg Thr Ser Pro Met Pro Gly His Pro Thr Ala Ser Pro
                405                 410                 415
Thr Ser Ser Glu Val Gln Gln Val Pro Ser Pro Val Ser Ser Glu Pro
            420                 425                 430
Pro Lys Ala Ala Arg Pro Pro Val Thr Pro Val Leu Leu Glu Lys Lys
        435                 440                 445
Ser Pro Leu Gly Gln Ser Gln Pro Thr Val Ala Gly Gln Pro Ser Ala
450                 455                 460
Arg Pro Ala Ala Glu Glu Tyr Gly Tyr Ile Val Thr Asp Gln Lys Pro
465                 470                 475                 480
Leu Ser Leu Ala Ala Gly Val Lys Leu Leu Glu Ile Leu Ala Glu His
                485                 490                 495
Val His Met Ser Ser Gly Ser Phe Ile Asn Ile Ser Val Val Gly Pro
            500                 505                 510
Ala Leu Thr Phe Arg Ile Arg His Asn Glu Gln Asn Leu Ser Leu Ala
        515                 520                 525
Asp Val Thr Gln Gln Ala Gly Leu Val Lys Ser Glu Leu Glu Ala Gln
        530                 535                 540
Thr Gly Leu Gln Ile Leu Gln Thr Gly Val Gly Gln Arg Glu Glu Ala
545                 550                 555                 560
Ala Ala Val Leu Pro Gln Thr Ala His Ser Thr Ser Pro Met Arg Ser
                565                 570                 575
Val Leu Leu Thr Leu Val Ala Leu Ala Gly Val Ala Gly Leu Leu Val
            580                 585                 590
Ala Leu Ala Val Ala Leu Cys Val Arg Gln His Ala Arg Gln Gln Asp
        595                 600                 605
Lys Glu Arg Leu Ala Ala Leu Gly Pro Glu Gly Ala His Gly Asp Thr
```

-continued

```
            610                 615                 620
Thr Phe Glu Tyr Gln Asp Leu Cys Arg Gln His Met Ala Thr Lys Ser
625                 630                 635                 640

Leu Phe Asn Arg Ala Glu Gly Pro Pro Glu Pro Ser Arg Val Ser Ser
                645                 650                 655

Val Ser Ser Gln Phe Ser Asp Ala Ala Gln Ala Ser Pro Ser Ser His
                660                 665                 670

Ser Ser Thr Pro Ser Trp Cys Glu Pro Ala Gln Ala Asn Met Asp
            675                 680                 685

Ile Ser Thr Gly His Met Ile Leu Ala Tyr Met Glu Asp His Leu Arg
690                 695                 700

Asn Arg Asp Arg Leu Ala Lys Glu Trp Gln Ala Leu Cys Ala Tyr Gln
705                 710                 715                 720

Ala Glu Pro Asn Thr Cys Ala Thr Ala Gln Gly Glu Gly Asn Ile Lys
                725                 730                 735

Lys Asn Arg His Pro Asp Phe Leu Pro Tyr Asp His Ala Arg Ile Lys
                740                 745                 750

Leu Lys Val Glu Ser Ser Pro Ser Arg Ser Asp Tyr Ile Asn Ala Ser
                755                 760                 765

Pro Ile Ile Glu His Asp Pro Arg Met Pro Ala Tyr Ile Ala Thr Gln
770                 775                 780

Gly Pro Leu Ser His Thr Ile Ala Asp Phe Trp Gln Met Val Trp Glu
785                 790                 795                 800

Ser Gly Cys Thr Val Ile Val Met Leu Thr Pro Leu Val Glu Asp Gly
                805                 810                 815

Val Lys Gln Cys Asp Arg Tyr Trp Pro Asp Glu Gly Ala Ser Leu Tyr
                820                 825                 830

His Val Tyr Glu Val Asn Leu Val Ser Glu His Ile Trp Cys Glu Asp
                835                 840                 845

Phe Leu Val Arg Ser Phe Tyr Leu Lys Asn Val Gln Thr Gln Glu Thr
850                 855                 860

Arg Thr Leu Thr Gln Phe His Phe Leu Ser Trp Pro Ala Glu Gly Thr
865                 870                 875                 880

Pro Ala Ser Thr Arg Pro Leu Leu Asp Phe Arg Arg Lys Val Asn Lys
                885                 890                 895

Cys Tyr Arg Gly Arg Ser Cys Pro Ile Ile Val His Cys Ser Asp Gly
                900                 905                 910

Ala Gly Arg Thr Gly Thr Tyr Ile Leu Ile Asp Met Val Leu Asn Arg
                915                 920                 925

Met Ala Lys Gly Val Lys Glu Ile Asp Ile Ala Ala Thr Leu Glu His
930                 935                 940

Val Arg Asp Gln Arg Pro Gly Leu Val Arg Ser Lys Asp Gln Phe Glu
945                 950                 955                 960

Phe Ala Leu Thr Ala Val Ala Glu Glu Val Asn Ala Ile Leu Lys Ala
                965                 970                 975

Leu Pro Gln
```

(2) INFORMATION FOR SEQ ID NO:6:

(i) SEQUENCE CHARACTERISTICS:
        (A) LENGTH: 585 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:6:

```
Met Ala Ser Pro Gly Ser Gly Phe Trp Ser Phe Gly Ser Glu Asp Gly
1               5                   10                  15

Ser Gly Asp Ser Glu Asn Pro Gly Thr Ala Arg Ala Trp Cys Gln Val
            20                  25                  30

Ala Gln Lys Phe Thr Gly Gly Ile Gly Asn Lys Leu Cys Ala Leu Leu
        35                  40                  45

Tyr Gly Asp Ala Glu Lys Pro Ala Glu Ser Gly Gly Ser Gln Pro Pro
    50                  55                  60

Arg Ala Ala Arg Lys Ala Ala Cys Ala Cys Asp Gln Lys Pro Cys
65                  70                  75                  80

Ser Cys Ser Lys Val Asp Val Asn Tyr Ala Phe Leu His Ala Thr Asp
                85                  90                  95

Leu Leu Pro Ala Cys Asp Gly Glu Arg Pro Thr Leu Ala Phe Leu Gln
            100                 105                 110

Asp Val Met Asn Ile Leu Leu Gln Tyr Val Val Lys Ser Phe Asp Arg
        115                 120                 125

Ser Thr Lys Val Ile Asp Phe His Tyr Pro Asn Glu Leu Leu Gln Glu
    130                 135                 140

Tyr Asn Trp Glu Leu Ala Asp Gln Pro Gln Asn Leu Glu Glu Ile Leu
145                 150                 155                 160

Met His Cys Gln Thr Thr Leu Lys Tyr Ala Ile Lys Thr Gly His Pro
                165                 170                 175

Arg Tyr Phe Asn Gln Leu Ser Thr Gly Leu Asp Met Val Gly Leu Ala
            180                 185                 190

Ala Asp Trp Leu Thr Ser Thr Ala Asn Thr Asn Met Phe Thr Tyr Glu
        195                 200                 205

Ile Ala Pro Val Phe Val Leu Leu Glu Tyr Val Thr Leu Lys Lys Met
    210                 215                 220

Arg Glu Ile Ile Gly Trp Pro Gly Gly Ser Gly Asp Gly Ile Phe Ser
225                 230                 235                 240

Pro Gly Gly Ala Ile Ser Asn Met Tyr Ala Met Met Ile Ala Arg Phe
                245                 250                 255

Lys Met Phe Pro Glu Val Lys Glu Lys Gly Met Ala Ala Leu Pro Arg
            260                 265                 270

Leu Ile Ala Phe Thr Ser Glu His Ser His Phe Ser Leu Lys Lys Gly
        275                 280                 285

Ala Ala Ala Leu Gly Ile Gly Thr Asp Ser Val Ile Leu Ile Lys Cys
    290                 295                 300

Asp Glu Arg Gly Lys Met Ile Pro Ser Asp Leu Glu Arg Arg Ile Leu
305                 310                 315                 320

Glu Ala Lys Gln Lys Gly Phe Val Pro Phe Leu Val Ser Ala Thr Ala
                325                 330                 335

Gly Thr Thr Val Tyr Gly Ala Phe Asp Pro Leu Leu Ala Val Ala Asp
            340                 345                 350

Ile Cys Lys Lys Tyr Lys Ile Trp Met His Val Asp Ala Ala Trp Gly
        355                 360                 365

Gly Gly Leu Leu Met Ser Arg Lys His Lys Trp Lys Leu Ser Gly Val
    370                 375                 380

Glu Arg Ala Asn Ser Val Thr Trp Asn Pro His Lys Met Met Gly Val
385                 390                 395                 400
```

```
Pro Leu Gln Cys Ser Ala Leu Leu Val Arg Glu Gly Leu Met Gln
                405                 410                 415

Asn Cys Asn Gln Met His Ala Ser Tyr Leu Phe Gln Gln Asp Lys His
                420                 425                 430

Tyr Asp Leu Ser Tyr Asp Thr Gly Asp Lys Ala Leu Gln Cys Gly Arg
                435                 440                 445

His Val Asp Val Phe Lys Leu Trp Leu Met Trp Arg Ala Lys Gly Thr
            450                 455                 460

Thr Gly Phe Glu Ala His Val Asp Lys Cys Leu Glu Leu Ala Glu Tyr
465                 470                 475                 480

Leu Tyr Asn Ile Ile Lys Asn Arg Glu Gly Tyr Glu Met Val Phe Asp
                485                 490                 495

Gly Lys Pro Gln His Thr Asn Val Cys Phe Trp Tyr Ile Pro Pro Ser
            500                 505                 510

Leu Arg Thr Leu Glu Asp Asn Glu Glu Arg Met Ser Arg Leu Ser Lys
            515                 520                 525

Val Ala Pro Val Ile Lys Ala Arg Met Met Glu Tyr Gly Thr Thr Met
545                 535                 540

Val Ser Tyr Gln Pro Leu Gly Asp Lys Val Asn Phe Phe Arg Met Val
545                 550                 555                 560

Ile Ser Asn Pro Ala Ala Thr His Gln Asp Ile Asp Phe Leu Ile Glu
                565                 570                 575

Glu Ile Glu Arg Leu Gly Gln Asp Leu
                580                 585

(2) INFORMATION FOR SEQ ID NO:7:

(i) SEQUENCE CHARACTERISTICS:
        (A) LENGTH: 110 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:7:

Met Ala Leu Trp Met Arg Leu Leu Pro Leu Leu Ala Leu Leu Ala Leu
1               5                   10                  15

Trp Gly Pro Asp Pro Ala Ala Ala Phe Val Asn Gln His Leu Cys Gly
                20                  25                  30

Ser His Leu Val Glu Ala Leu Tyr Leu Val Cys Gly Glu Arg Gly Phe
            35                  40                  45

Phe Tyr Thr Pro Lys Thr Arg Arg Glu Ala Glu Asp Leu Gln Val Gly
        50                  55                  60

Gln Val Glu Leu Gly Gly Gly Pro Gly Ala Gly Ser Leu Gln Pro Leu
65                  70                  75                  80

Ala Leu Glu Gly Ser Leu Gln Lys Arg Gly Ile Val Glu Gln Cys Cys
                85                  90                  95

Thr Ser Ile Cys Ser Leu Tyr Gln Leu Glu Asn Tyr Cys Asn
                100                 105                 110

(2) INFORMATION FOR SEQ ID NO:8:

(i) SEQUENCE CHARACTERISTICS:
        (A) LENGTH: 2457 base pairs
        (B) TYPE: nucleic acid
        (C) STRANDEDNESS: double
        (D) TOPOLOGY: linear
```

(ii) MOLECULE TYPE: cDNA (xi) SEQUENCE DESCRIPTION: SEQ ID NO:8:

| | | | | | |
|---|---|---|---|---|---|
| ACCCGCCCTC | GCCGCTCGGC | CCCGCGCGTC | CCCGCGCGTG | CCCTCCTCCC | GCCACACGGC | 60
| ACGCACGCGC | GCGCAGGGCC | AAGCCGAGGC | AGCCGCCCGC | AGCTCGCACT | CGCTGGCGAC | 120
| CTGCTCCAGT | CTCCAAAGCC | GATGGCATCT | CCGGGCTCTG | GCTTTTGGTC | TTTCGGGTCG | 180
| GAAGATGGCT | CTGGGGATTC | CGAGAATCCC | GGCACAGCGC | GAGCCTGGTG | CCAAGTGGCT | 240
| CAGAAGTTCA | CGGGCGGCAT | CGGAAACAAA | CTGTGCGCCC | TGCTCTACGG | AGACGCCGAG | 300
| AAGCCGGCGG | AGAGCGGCGG | GAGCCAACCC | CGCGGGCCG | CCGCCCGGAA | GGCCGCCTGC | 360
| GCCTGCGACC | AGAAGCCCTG | CAGCTGCTCC | AAAGTGGATG | TCAACTACGC | GTTTCTCCAT | 420
| GCAACAGACC | TGCTGCCGGC | GTGTGATGGA | GAAAGGCCCA | CTTTGGCGTT | TCTGCAAGAT | 480
| GTTATGAACA | TTTTACTTCA | GTATGTGGTG | AAAAGTTTCG | ATAGATCAAC | CAAAGTGATT | 540
| GATTTCCATT | ATCCTAATGA | GCTTCTCCAA | GAATATAATT | GGGAATTGGC | AGACCAACCA | 600
| CAAAATTTGG | AGGAAATTTT | GATGCATTGC | CAAACAACTC | TAAAATATGC | AATTAAAACA | 660
| GGGCATCCTA | GATACTTCAA | TCAACTTTCT | ACTGGTTTGG | ATATGGTTGG | ATTAGCAGCA | 720
| GACTGGCTGA | CATCAACAGC | AAATACTAAC | ATGTTCACCT | ATGAAATTGC | TCCAGTATTT | 780
| GTGCTTTTGG | AATATGTCAC | ACTAAAGAAA | ATGAGAGAAA | TCATTGGCTG | GCCAGGGGC | 840
| TCTGGCGATG | GGATATTTTC | TCCCGGTGGC | GCCATATCTA | ACATGTATGC | CATGATGATC | 900
| GCACGCTTTA | GATGTTCCC | AGAAGTCAAG | GAGAAAGGAA | TGGCTGCTCT | TCCCAGGCTC | 960
| ATTGCCTTCA | CGTCTGAACA | TAGTCATTTT | TCTCTCAAGA | AGGGAGCTGC | AGCCTTAGGG | 1020
| ATTGGAACAG | ACAGCGTGAT | TCTGATTAAA | TGTGATGAGA | GAGGGAAAAT | GATTCCATCT | 1080
| GATCTTGAAA | GAAGGATTCT | TGAAGCCAAA | CAGAAAGGGT | TTGTTCCTTT | CCTCGTGAGT | 1140
| GCCACAGCTG | GAACCACCGT | GTACGGAGCA | TTTGACCCCC | TCTTAGCTGT | CGCTGACATT | 1200
| TGCAAAAAGT | ATAAGATCTG | GATGCATGTG | GATGCAGCTT | GGGGTGGGGG | ATTACTGATG | 1260
| TCCCGAAAAC | ACAAGTGGAA | ACTGAGTGGC | GTGGAGAGGG | CCAACTCTGT | GACGTGGAAT | 1320
| CCACACAAGA | TGATGGGAGT | CCCTTTGCAG | TGCTCTGCTC | TCCTGGTTAG | AGAAGAGGGA | 1380
| TTGATGCAGA | ATTGCAACCA | AATGCATGCC | TCCTACCTCT | TTCAGCAAGA | TAAACATTAT | 1440
| GACCTGTCCT | ATGACACTGG | AGACAAGGCC | TTACAGTGCG | GACGCCACGT | TGATGTTTTT | 1500
| AAACTATGGC | TGATGTGGAG | GGCAAAGGGG | ACTACCGGGT | TGAAGCGCA | TGTTGATAAA | 1560
| TGTTTGGAGT | TGGCAGAGTA | TTTATACAAC | ATCATAAAAA | ACCGAGAAGG | ATATGAGATG | 1620
| GTGTTTGATG | GGAAGCCTCA | GCACACAAAT | GTCTGCTTCT | GGTACATTCC | TCCAAGCTTG | 1680
| CGTACTCTGG | AAGACAATGA | AGAGAGAATG | AGTCGCCTCT | CGAAGGTGGC | TCCAGTGATT | 1740
| AAAGCCAGAA | TGATGGAGTA | TGGAACCACA | ATGGTCAGCT | ACCAACCCTT | GGGAGACAAG | 1800
| GTCAATTTCT | TCCGCATGGT | CATCTCAAAC | CCAGCGGCAA | CTCACCAAGA | CATTGACTTC | 1860
| CTGATTGAAG | AAATAGAACG | CCTTGGACAA | GATTTATAAT | AACCTTGCTC | ACCAAGCTGT | 1920
| TCCACTTCTC | TAGAGAACAT | GCCCTCAGCT | AAGCCCCCTA | CTGAGAAACT | TCCTTTGAGA | 1980
| ATTGTGCGAC | TTCACAAAAT | GCAAGGTGAA | CACCACTTTG | TCTCTGAGAA | CAGACGTTAC | 2040
| CAATTATGGA | GTGTCACCAG | CTGCCAAAAT | CGTAGGTGTT | GGCTCTGCTG | GTCACTGGAG | 2100
| TAGTTGCTAC | TCTTCAGAAT | ATGGACAAAG | AAGGCACAGG | TGTAAATATA | GTAGCAGGAT | 2160
| GAGGAACCTC | AAACTGGGTA | TCATTTGCAC | GTGCTCTTCT | GTTCTCAAAT | GCTAAATGCA | 2220
| AACACTGTGT | ATTTATTAGT | TAGGTGTGCC | AAACTACCGT | TCCCAAATTG | GTGTTTCTGA | 2280

| | |
|---|---|
| ATGACATCAA CATTCCCCCA ACATTACTCC ATTACTAAAG ACAGAAAAAA ATAAAAACAT | 2340 |
| AAAATATACA AACATGTGGC AACCTGTTCT TCCTACCAAA TATAAACTTG TGTATGATCC | 2400 |
| AAGTATTTTA TCTGTGTTGT CTCTCTAAAC CCAAATAAAT GTGTAAATGT GGACACA | 2457 |

(2) INFORMATION FOR SEQ ID NO:9:

(i) SEQUENCE CHARACTERISTICS:
        (A) LENGTH: 3613 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:9:

| | |
|---|---|
| CAGCCCCTCT GGCAGGCTCC CGCCAGCGTC GCTGCGGCTC CGGCCCGGGA GCGAGCGCCC | 60 |
| GGAGCTCGGA AAGATGCGGC GCCCGCGGCG GCCTGGGGGT CTCGGGGGAT CCGGGGGTCT | 120 |
| CCGGCTGCTC CTCTGCCTCC TGCTGCTGAG CAGCCGCCCG GGGGCTGCA GCGCCGTTAG | 180 |
| TGCCCACGGC TGTCTATTTG ACCGCAGGCT CTGCTCTCAC CTGGAAGTCT GTATTCAGGA | 240 |
| TGGCTTGTTT GGGCAGTGCC AGGTGGGAGT GGGGCAGGCC CGGCCCCTTT TGCAAGTCAC | 300 |
| CTCCCCAGTT CTCCAACGCT TACAAGGTGT GCTCCGACAA CTCATGTCCC AAGGATTGTC | 360 |
| CTGGCACGAT GACCTCACCC AGTATGTGAT CTCTCAGGAG ATGGAGCGCA TCCCCAGGCT | 420 |
| TCGCCCCCCA GAGCCCCGTC AAGGGACAG GTCTGGCTTG CACCCAAGA GACCTGGTCC | 480 |
| TGCTGGAGAG CTGCTTTTAC AGGACATCCC CACTGGCTCC GCCCCTGCTG CCCAGCATCG | 540 |
| GCTTCCACAA CCACCAGTGG GCAAAGGTGG AGCTGGGGCC AGCTCCTCTC TGTCCCCTCT | 600 |
| GCAGGCTGAG CTGCTCCCGC CTCTCTTGGA GCACCTGCTG CTGCCCCCAC AGCCTCCCCA | 660 |
| CCCTTCACTG AGTTACGAAC CTGCCTTGCT GCAGCCCTAC CTGTTCCACC AGTTTGGCTC | 720 |
| CCGTGATGGC TCCAGGGTCT CAGAGGGCTC CCCAGGGATG GTCAGTGTCG GCCCCCTGCC | 780 |
| CAAGGCTGAA GCCCCTGCCC TCTTCAGCAG AACTGCCTCC AAGGGCATAT TTGGGGACCA | 840 |
| CCCTGGCCAC TCCTACGGGG ACCTTCCAGG GCCTTCACCT GCCCAGCTTT TTCAAGACTC | 900 |
| TGGGCTGCTC TATCTGGCCC AGGAGTTGCC AGCACCCAGC AGGGCCAGGG TGCCAAGGCT | 960 |
| GCCAGAGCAA GGGAGCAGCA GCCGGGCAGA GGACTCCCCA GAGGGCTATG AGAAGGAAGG | 1020 |
| ACTAGGGGAT CGTGGAGAGA AGCCTGCTTC CCCAGCTGTG CAGCCAGATG CGGCTCTGCA | 1080 |
| GAGGCTGGCC GCTGTGCTGG CGGGCTATGG GGTAGAGCTG CGTCAGCTGA CCCCTGAGCA | 1140 |
| GCTCTCCACA CTCCTGACCC TGCTGCAGCT ACTGCCCAAG GGTGCAGGAA GAAATCCGGG | 1200 |
| AGGGGTTGTA AATGTTGGAG CTGATATCAA GAAAACAATG GAGGGGCCGG TGGAGGGCAG | 1260 |
| AGACACAGCA GAGCTTCCAG CCCGCACATC CCCCATGCCT GGACACCCCA CTGCCAGCCC | 1320 |
| TACCTCCAGT GAAGTCCAGC AGGTGCCAAG CCCTGTCTCC TCTGAGCCTC CCAAAGCTGC | 1380 |
| CAGACCCCCT GTGACACCTG TCCTGCTAGA GAAGAAAAGC CCACTGGGCC AGAGCCAGCC | 1440 |
| CACGGTGGCA GGACAGCCCT CAGCCCGCCC AGCAGCAGAG GAATATGGCT ACATCGTCAC | 1500 |
| TGATCAGAAG CCCCTGAGCC TGGCTGCAGG AGTGAAGCTG CTGGAGATCC TGGCTGAGCA | 1560 |
| TGTGCACATG TCCTCAGGCA GCTTCATCAA CATCAGTGTG GTGGGACCAG CCCTCACCTT | 1620 |
| CCGCATCCGG CACAATGAGC AGAACCTGTC TTTGGCTGAT GTGACCCAAC AAGCAGGGCT | 1680 |
| GGTGAAGTCT GAACTGGAAG CACAGACAGG GCTCCAAATC TTGCAGACAG GAGTGGGACA | 1740 |
| GAGGGAGGAG GCAGCTGCAG TCCTTCCCCA AACTGCGCAC AGCACCTCAC CCATGCGCTC | 1800 |

```
AGTGCTGCTC ACTCTGGTGG CCCTGGCAGG TGTGGCTGGG CTGCTGGTGG CTCTGGCTGT    1860

GGCTCTGTGT GTGCGGCAGC ATGCGCGGCA GCAAGACAAG GAGCGCCTGG CAGCCCTGGG    1920

GCCTGAGGGG GCCCATGGTG ACACTACCTT TGAGTACCAG GACCTGTGCC GCCAGCACAT    1980

GGCCACGAAG TCCTTGTTCA ACCGGGCAGA GGGTCCACCG GAGCCTTCAC GGGTGAGCAG    2040

TGTGTCCTCC CAGTTCAGCG ACGCAGCCCA GGCCAGCCCC AGCTCCCACA GCAGCACCCC    2100

GTCCTGGTGC GAGGAGCCGG CCCAAGCCAA CATGGACATC TCCACGGGAC ACATGATTCT    2160

GGCATACATG GAGGATCACC TGCGGAACCG GGACCGCCTT GCCAAGGAGT GGCAGGCCCT    2220

CTGTGCCTAC CAAGCAGAGC CAAACACCTG TGCCACCGCG CAGGGGGAGG GCAACATCAA    2280

AAAGAACCGG CATCCTGACT TCCTGCCCTA TGACCATGCC CGCATAAAAC TGAAGGTGGA    2340

GAGCAGCCCT TCTCGGAGCG ATTACATCAA CGCCAGCCCC ATTATTGAGC ATGACCCTCG    2400

GATGCCAGCC TACATAGCCA CGCAGGGCCC GCTGTCCCAT ACCATCGCAG ACTTCTGGCA    2460

GATGGTGTGG GAGAGCGGCT GCACCGTCAT CGTCATGCTG ACCCCGCTGG TGGAGGATGG    2520

TGTCAAGCAG TGTGACCGCT ACTGGCCAGA TGAGGGTGCC TCCCTCTACC ACGTATATGA    2580

GGTGAACCTG GTGTCGGAGC ACATCTGGTG CGAGGACTTT CTGGTGCGGA GCTTCTACCT    2640

GAAGAACGTG CAGACCCAGG AGACGCGCAC GCTCACGCAG TTCCACTTCC TCAGCTGGCC    2700

GGCAGAGGGC ACACCGGCCT CCACGCGGCC CCTGCTGGAC TTCCGCAGGA AGGTGAACAA    2760

GTGCTACCGG GGCCGCTCCT GCCCCATCAT CGTGCACTGC AGTGATGGTG CGGGGAGGAC    2820

CGGCACCTAC ATCCTCATCG ACATGGTCCT GAACCGCATG GCAAAAGGAG TGAAGGAGAT    2880

TGACATCGCT GCCACCCTGG AGCATGTCCG TGACCAGCGG CCTGGCCTTG TCCGCTCTAA    2940

GGACCAGTTT GAATTTGCCC TGACAGCCGT GGCGGAGGAA GTGAATGCCA TCCTCAAGGC    3000

CCTGCCCCAG TGAGACCCTG GGGCCCCTTG GCGGGCAGCC CAGCCTCTGT CCCTCTTTGC    3060

CTGTGTGAGC ATCTCTGTGT ACCCACTCCT CACTGCCCCA CCAGCCACCT CTTGGGCATG    3120

CTCAGCCCTT CCTAGAAGAG TCAGGAAGGG AAAGCCAGAA GGGGCACGCC TGCCCAGCCT    3180

CGCATGCCAG AGCCTGGGGC ATCCCAGAGC CCAGGGCATC CCATGGGGGT GCTGCAGCCA    3240

GGAGGAGAGG AAAGGACATG GGTAGCAATT CTACCCAGAG CCTTCTCCTG CCTACATTCC    3300

CTGGCCTGGC TCTCCTGTAG CTCTCCTGGG GTTCTGGGAG TTCCCTGAAC ATCTGTGTGT    3360

GTCCCCCTAT GCTCCAGTAT GGAAGAATGG GGTGGAGGGT CGCCACACCC GGCTCCCCCT    3420

GCTTCTCAGC CCCGGGCCTG CCTCTGACTC ACACTTGGGC GCTCTGCCCT CCCTGGCCTC    3480

ACGCCCAGCC TGGTCCCACC ACCCTCCCAC CATGCGCTGC TCAACCTCTC TCCTTCTGGC    3540

GCAAGAGAAC ATTTCTAGAA AAAACTACTT TTGTACCAGT GTGAATAAAG TTAGTGTGTT    3600

GTCTGTGCAG CTG                                                       3613
```

(2) INFORMATION FOR SEQ ID NO:10:

(i) SEQUENCE CHARACTERISTICS:
        (A) LENGTH: 4992 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

```
CTCGAGGGGC CTAGACATTG CCCTCCAGAG AGAGCACCCA ACACCCTCCA GGCTTGACCG      60

GCCAGGGTGT CCCCTTCCTA CCTTGGAGAG AGCAGCCCCA GGGCATCCTG CAGGGGGTGC     120
```

-continued

```
TGGGACACCA GCTGGCCTTC AAGGTCTCTG CCTCCCTCCA GCCACCCCAC TACACGCTGC    180
TGGGATCCTG GATCTCAGCT CCCTGGCCGA CAACACTGGC AAACTCCTAC TCATCCACGA    240
AGGCCCTCCT GGGCATGGTG GTCCTTCCCA GCCTGGCAGT CTGTTCCTCA CACACCTTGT    300
TAGTGCCCAG CCCCTGAGGT TGCAGCTGGG GGTGTCTCTG AAGGGCTGTG AGCCCCAGG     360
AAGCCCTGGG GAAGTGCCTG CCTTGCCTCC CCCCGGCCCT GCCAGCGCCT GGCTCTGCCC    420
TCCTACCTGG GCTCCCCCCA TCCAGCCTCC CTCCCTACAC ACTCCTCTCA AGGAGGCACC    480
CATGTCCTCT CCAGCTGCCG GGCCTCAGAG CACTGTGGCG TCCTGGGGCA GCCACCGCAT    540
GTCCTGCTGT GGCATGGCTC AGGGTGGAAA GGGCGGAAGG GAGGGGTCCT GCAGATAGCT    600
GGTGCCCACT ACCAAACCCG CTCGGGGCAG AGAGCCAAA GGCTGGGTGT GTGCAGAGCG     660
GCCCCGAGAG GTTCCGAGGC TGAGGCCAGG GTGGGACATA GGGATGCGAG GGGCCGGGGC    720
ACAGGATACT CCAACCTGCC TGCCCCCATG GTCTCATCCT CCTGCTTCTG GGACCTCCTG    780
ATCCTGCCCC TGGTGCTAAG AGGCAGGTAA GGGGCTGCAG GCAGCAGGGC TCGGAGCCCA    840
TGCCCCCTCA CCATGGGTCA GGCTGGACCT CCAGGTGCCT GTTCTGGGGA GCTGGGAGGG    900
CCGGAGGGGT GTACCCCAGG GGCTCAGCCC AGATGACACT ATGGGGGTGA TGGTGTCATG    960
GGACCTGGCC AGGAGAGGGG AGATGGGCTC CCAGAAGAGG AGTGGGGGCT GAGAGGGTGC   1020
CTGGGGGGCC AGGACGGAGC TGGGCCAGTG CACAGCTTCC CACACCTGCC CACCCCCAGA   1080
GTCCTGCCGC CACCCCCAGA TCACACGGAA GATGAGGTCC GAGTGGCCTG CTGAGGACTT   1140
GCTGCTTGTC CCCAGGTCCC CAGGTCATGC CCTCCTTCTG CCACCCTGGG GAGCTGAGGG   1200
CCTCAGCTGG GGCTGCTGTC CTAAGGCAGG GTGGGAACTA GGCAGCCAGC AGGGAGGGGA   1260
CCCCTCCCTC ACTCCCACTC TCCCACCCCC ACCACCTTGG CCCATCCATG GCGGCATCTT   1320
GGGCCATCCG GGACTGGGGA CAGGGTCCT GGGGACAGGG GTCCGGGGAC AGGGTCCTGG    1380
GGACAGGGGT GTGGGACAG GGGTCTGGGG ACAGGGGTGT GGGGACAGGG GTGTGGGGAC    1440
AGGGGTCTGG GGACAGGGGT GTGGGGACAG GGGTCCGGGG ACAGGGGTGT GGGGACAGGG   1500
GTCTGGGGAC AGGGGTGTGG GGACAGGGGT GTGGGGACAG GGGTCTGGGG ACAGGGGTGT   1560
GGGGACAGGG GTCCTGGGGA CAGGGGTGTG GGGACAGGGG TGTGGGGACA GGGGTGTGGG   1620
GACAGGGGTG TGGGGACAGG GGTCCTGGGG ATAGGGGTGT GGGGACAGGG GTGTGGGGAC   1680
AGGGGTCCCG GGGACAGGGG TGTGGGGACA GGGGTGTGGG GACAGGGGTC CTGGGGACAG   1740
GGGTCTGAGG ACAGGGGTGT GGGCACAGGG GTCCTGGGGA CAGGGGTCCT GGGGACAGGG   1800
GTCCTGGGGA CAGGGGTCTG GGGACAGCAG CGCAAAGAGC CCCGCCCTGC AGCCTCCAGC   1860
TCTCCTGGTC TAATGTGGAA AGTGGCCCAG GTGAGGGCTT TGCTCTCCTG GAGACATTTG   1920
CCCCCAGCTG TGAGCAGGGA CAGGTCTGGC CACCGGGCCC CTGGTTAAGA CTCTAATGAC   1980
CCGCTGGTCC TGAGGAAGAG GTGCTGACGA CCAAGGAGAT CTTCCCACAG ACCCAGCACC   2040
AGGGAAATGG TCCGGAAATT GCAGCCTCAG CCCCCAGCCA TCTGCCGACC CCCCACCCC    2100
GCCCTAATGG GCCAGGCGGC AGGGGTTGAC AGGTAGGGGA GATGGGCTCT GAGACTATAA   2160
AGCCAGCGGG GGCCCAGCAG CCCTCAGCCC TCCAGGACAG GCTGCATCAG AAGAGGCCAT   2220
CAAGCAGGTC TGTTCCAAGG GCCTTTGCGT CAGGTGGGCT CAGGGTTCCA GGGTGGCTGG   2280
ACCCCAGGCC CCAGCTCTGC AGCAGGGAGG ACGTGGCTGG GCTCGTGAAG CATGTGGGGG   2340
TGAGCCCAGG GGCCCAAGG CAGGGCACCT GGCCTTCAGC CTGCCTCAGC CCTGCCTGTC    2400
TCCCAGATCA CTGTCCTTCT GCCATGGCCC TGTGGATGCG CCTCCTGCCC CTGCTGGCGC   2460
```

```
TGCTGGCCCT CTGGGGACCT GACCCAGCCG CAGCCTTTGT GAACCAACAC CTGTGCGGCT    2520
CACACCTGGT GGAAGCTCTC TACCTAGTGT GCGGGGAACG AGGCTTCTTC TACACACCCA    2580
AGACCCGCCG GGAGGCAGAG GACCTGCAGG GTGAGCCAAC CGCCCATTGC TGCCCCTGGC    2640
CGCCCCCAGC CACCCCCTGC TCCTGGCGCT CCCACCCAGC ATGGGCAGAA GGGGGCAGGA    2700
GGCTGCCACC CAGCAGGGGG TCAGGTGCAC TTTTTTAAAA AGAAGTTCTC TTGGTCACGT    2760
CCTAAAAGTG ACCAGCTCCC TGTGGCCCAG TCAGAATCTC AGCCTGAGGA CGGTGTTGGC    2820
TTCGGCAGCC CCGAGATACA TCAGAGGGTG GGCACGCTCC TCCCTCCACT CGCCCCTCAA    2880
ACAAATGCCC CGCAGCCCAT TTCTCCACCC TCATTTGATG ACCGCAGATT CAAGTGTTTT    2940
GTTAAGTAAA GTCCTGGGTG ACCTGGGGTC ACAGGGTGCC CCACGCTGCC TGCCTCTGGG    3000
CGAACACCCC ATCACGCCCG GAGGAGGGCG TGGCTGCCTG CCTGAGTGGG CCAGACCCCT    3060
GTCGCCAGCC TCACGGCAGC TCCATAGTCA GGAGATGGGG AAGATGCTGG GGACAGGCCC    3120
TGGGGAGAAG TACTGGGATC ACCTGTTCAG GCTCCCACTG TGACGCTGCC CCGGGGCGGG    3180
GGAAGGAGGT GGGACATGTG GGCGTTGGGG CCTGTAGGTC CACACCCAGT GTGGGTGACC    3240
CTCCCTCTAA CCTGGGTCCA GCCCGGCTGG AGATGGGTGG GAGTGCGACC TAGGGCTGGC    3300
GGGCAGGCGG GCACTGTGTC TCCCTGACTG TGTCCTCCTG TGTCCCTCTG CCTCGCCGCT    3360
GTTCCGGAAC CTGCTCTGCG CGGCACGTCC TGGCAGTGGG GCAGGTGGAG CTGGGCGGGG    3420
GCCCTGGTGC AGGCAGCCTG CAGCCCTTGG CCCTGGAGGG GTCCCTGCAG AAGCGTGGCA    3480
TTGTGGAACA ATGCTGTACC AGCATCTGCT CCCTCTACCA GCTGGAGAAC TACTGCAACT    3540
AGACGCAGCC TGCAGGCAGC CCCACACCCG CCGCCTCCTG CACCGAGAGA GATGGAATAA    3600
AGCCCTTGAA CCAGCCCTGC TGTGCCGTCT GTGTGTCTTG GGGGCCCTGG GCCAAGCCCC    3660
ACTTCCCGGC ACTGTTGTGA GCCCCTCCCA GCTCTCTCCA CGCTCTCTGG GTGCCCACAG    3720
GTGCCAACGC CAGGCAGGCC CAGCATGCAG TGGCTCTCCC CAAAGCGGCC ATGCCTGTTG    3780
GCTGCCTGCT GCCCCCACCC TGTGGCTCAG GGTCCAGTAT GGGAGCTTCG GGGGTCTCTG    3840
AGGGGCCAGG GATGGTGGGG CCACTGAGAA GTGACTCTGT CAGTAGCCGA CCTGGAGTCC    3900
CCAGAGACCT TGTTCAGGAA AGGGAATGAG AACATTCCAG CAATTTTCCC CCCACCTAGC    3960
CCTCCCAGGT TCTATTTTTA GAGTTATTTC TGATGGAGTC CCTGTGGAGG GAGGAGGCTG    4020
GGCTGAGGGA GGGGGTCCTG CAGGGCGGGG GGCTGGGAAG GTGGGGAGAG GCTGCCGAGA    4080
GCCACCCGCT ATCCCCAGCT CTGGGCAGCC CCGGGACAGT CACACACCCT GGCCTCGCGG    4140
CCCAAGCTGG CAGCCGTCTG CAGCCACAGC TTATGCCAGC CCAGGTCCAG CCAGACACCT    4200
GAGGGACCCA CTGGTGCCTT GGAGGAAGCA GGAGAGGTCA GATGGCACCA TGAGCTGGGG    4260
CAGGTGCAGG GACCGTGGCA GCACCTGGCA GGGCCTCAGA ACCCATGCCT TGGGCACCCC    4320
GGCCATGAGG CCCTGAGGAT TGCAGCCCAA GAGAAGCAGG GAACGCCAGG GCCACAGGGG    4380
CAGAGACCAG GCCAGGGTCC CTTGCGGCCC TTAGCCCACC CCCTCCCAGT AAGCAGGGGC    4440
TGCTTGGCTA GGCTTCCTTT TGCTACAGAC CTGCTGCTCA CCCAGAGGCC CACGGGCCCT    4500
AGTGACAAGG TCGTTGTGGC TCCAGGTCCT TGGGGGTCCT GACACAGAGC CTCTTCTGCA    4560
GCACCCCTGA GGACAGGGTG CTCCGCTGGG CACCCAGCCT AGTGGGCAGA CGAGAACCTA    4620
GGGGCTGCCT GGGCCTACTG TGGCCTGGGA GGTCAGCGGG TGACCCTAGC TACCCTGTGG    4680
CTGGGCCAGT CTGCCTGCCA CCCAGGCCAA ACCAATCTGC ACCTTTCCTG AGAGCTCCAC    4740
CCAGGGCTGG GCTGGGGATG GCTGGGCCTG GGGCTGGCAT GGGCTGTGGC TGCAGACCAC    4800
TGCCAGCTTG GGCCTCGAGG CCAGGAGCTC ACCCTCCAGC TGCCCCGCCT CCAGAGTGGG    4860
```

```
GGCCAGGGCT GGGCAGGCGG GTGGACGGCC GGACACTGGC CCCGGAAGAG GAGGGAGGCG    4920

GTGGCTGGGA TCGGCAGCAG CCGTCCATGG GAACACCCAG CCGGCCCCAC TCGCACGGGT    4980

AGAGACAGGC GC                                                        4992

(2) INFORMATION FOR SEQ ID NO:11:

(i) SEQUENCE CHARACTERISTICS:
        (A) LENGTH: 10 amino acids
        (B) TYPE: amino acid
        (C) STRANDEDNESS:
        (D) TOPOLOGY: linear (ii) MOLECULE TYPE: peptide (v) FRAGMENT TYPE: C-terminal (xi) SEQUENCE DESCRIPTION: SEQ ID NO:11:

Xaa Xaa Gly Ser His His His His His His
1               5                   10

(2) INFORMATION FOR SEQ ID NO:12:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA for bridge peptide"

(xi) SEQUENCE DESCRIPTION: SEQ ID NO:12:

AAGAAGAAGC GGCCGCGAAA GAAGAAG                                          27

(2) INFORMATION FOR SEQ ID NO:13:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA for bridge peptide"

(xi) SEQUENCE DESCRIPTION: SEQ ID NO:13:

AAGAAGAAGC GATCGCGAAA GAAGAAG                                          27
```

FUSION PROTEIN AND ITS USE IN AN IMMUNOASSAY FOR THE SIMULTANEOUS DETECTION OF AUTOANTIBODIES RELATED TO INSULIN-DEPENDENT DIABETES MELLITUS

FIELD OF THE INVENTION

This invention relates to a new fusion protein, its cDNA, and a vector and a cell comprising said cDNA. Furthermore, this invention relates to the use of said fusion protein in an immunoassay for simultaneous detection of autoantibodies related to insulin dependent diabetes mellitus.

BACKGROUND OF THE INVENTION

The publications and other materials used herein to illuminate the background of the invention, and in particular, cases to provide additional details respecting the practice, are incorporated by reference.

GAD65, IA2 and insulin are pancreatic proteins produced by the beta cells (for review see Atkinson and Maclaren 1993). Autoantibodies to these proteins are detected in patients with insulin-dependent diabetes mellitus (IDDM) and healthy individuals at risk for developing the disease. More than 80% of newly-diagnosed IDDM patients have antibodies against at least one of these proteins (Baekkeskov et al. 1982). The risk of diabetes in relatives of IDDM patients increases markedly when the number of autoantibodies detected in the serum increases (Bingley et al. 1994; Verge et al. 1994). In a group of high genetic risk, presence in serum of antibodies to one or more of these autoantigens predicted the disease onset accurately (Verge et al. 1996). Also permanently healthy subjects (as regards IDDM) may have temporarily or permanently antibodies against one of the three antigens, but antibodies against multiple antigens occur extremely rarely. It is therefore sought to simultaneously determine reactivity against two or all three of the proteins, as the positivity for more than one of these autoantibodies remarkably increases disease risk (Bingley et al. 1994).

GAD65 (Bu et al. 1992) has several epitopes recognised by autoantibodies (Falorni et al. 1996). These are located mostly at the center and C-terminus of the molecule whereas the N-terminal quarter of the molecule is thought to contribute to membrane docking of the protein, and to contain few if any IDDM-informative epitopes (Falorni et al. 1996).

IA2 (also known as ICA512) (Rabin et al. 1994) is a transmembrane protein with still unknown function. The intracellular part of the molecule ($IA2_{ic}$, about 40 kDa) contains a domain with similarity to the active center of protein phosphatases (Fischer et al. 1991), but no enzymatic activity has been ascribed the IA2 molecule. The informative epitopes of IA2 reside in the cytoplasmic domain and herein they are concentrated at the C-terminal half (Lampasona et al. 1996; Zhang et al. 1997).

Insulin (Bell et al. 1980) is made by pancreatic β-cells as a precursor preproinsulin which is cleaved to proinsulin. The proinsulin is further processed to give the insulin consisting of A and B chains connected together with two disulphide bridges.

More than 20% of sera collected from newly-diagnosed IDDM-patients contain insulin autoantibodies (IAA) (Sabbah et al. 1996). As, however, the immunity to insulin may have arisen through formation of response to prepro- or proinsulins (Snorgaard et al. 1996), it is relevant to use these peptides in this assay system. Tolerance to this autoantigen may be induced by oral insulin feeding in non-obese diabetic (NOD) mice (Zhang et al. 1991).

In addition to linear epitopes, autoantibodies are thought to recognize important conformational epitopes resulting from the three-dimensional structure of the protein (Kim et al. 1993). Antigen molecules produced or assayed using techniques which destroy these structures are less informative as regards IDDM or prediabetes.

Several methods for detection of autoantibodies in IDDM sera have been elaborated. One method exploits in vitro transcription-translation for producing radioactively labeled autoantigen (IA2, GAD65) (Petersen et al. 1994), while in another method biotin-labeled GAD65 is added to the patient sera and after formation of immune complexes, free label is detected and quantitated (Mehta et al. 1996). These methods all suffer from suboptimal niveau of informativity, as they employ only one specific autoantigen. Moreover they have the drawbacks associated with the use of radiochemicals.

Using a protein molecule in which a combination of the epitopes from at least two but preferably three different autoantigens are represented should detect a larger panel of autoantibodies thus revealing more specifically the population of individuals at risk of developing the disease.

SUMMARY OF THE INVENTION

According to one aspect, this invention relates to a new fusion protein having epitopes of at least two of the autoantigens glutamic acid decarboxylase (GAD65), islet cell antigen (IA2) and preproinsulin (PPINS) wherein said epitopes are connected with a linker peptide, said fusion protein being able to bind to a solid phase.

According to another aspect, the invention concerns a cDNA sequence encoding the said fusion protein.

According to a third aspect, the invention concerns a vector and a cell comprising said cDNA.

According to a fourth aspect, the invention concerns an immunoassay for the simultaneous determination in a sample of a person's body fluid of at least two insulin-dependent diabetes mellitus (IDDM)-related autoantibodies, wherein each autoantibody is specific for an epitope of the autoantigens glutamic acid decarboxylase (GAD65), islet cell antigen (IA2) or preproinsulin (PPINS). The immunoassay comprises the steps of incubating said sample with said autoantigens or, alternatively, with the fusion protein according to this invention, said autoantigens or said fusion protein being bound to a solid support, adding at least one labeled reagent capable of binding to one or more of said autoantibodies, and quantifying the signals from the labels bound to the solid phase.

According to still one aspect, the invention concerns a method for diagnosing a person's risk of developing insulin-dependent diabetes mellitus (IDDM), said method comprising the determination in a sample of said person's body fluid of at least two insulin dependent diabetes mellitus (IDDM)-related autoantibodies specific for an epitope of the autoantigens glutamic acid decarboxylase (GAD65), islet cell antigen (IA2) or preproinsulin (PPINS), wherein the presence of at least two of said autoantibodies are indicative for said person's risk of developing IDDM. The order of appearance of these autoantibodies is used to predict the time point of onset of the disease.

BRIEF DESCRIPTION OF THE DRAWINGS

FIGS. 1a and 1b show the cDNA construct for a fusion protein according to this invention (flag peptide (SEQ ID NO:1); NotI (SEQ ID NO:2); poly-his (SEQ ID NO:3) and SgfI (SEQ ID NO:4)), FIG. 2a shows the amino acid sequence of the IA2 protein (SEQ ID NO:5), FIG. 2b shows the amino acid sequence of the GAD65 protein (SEQ ID NO:6), FIG. 2c shows the amino acid sequence of preproinsulin (PPINS) (SEQ ID NO:7), FIGS. 3a–3b show the nucleotide sequence encoding GAD65 (SEQ ID NO:8), FIGS. 3c–3e show the nucleotide sequence encoding IA2 (SEQ ID NO:9), FIGS. 3f–3i show the human insulin gene (SEQ ID NO:10)

DETAILED DESCRIPTION OF THE INVENTION

Figure 4:
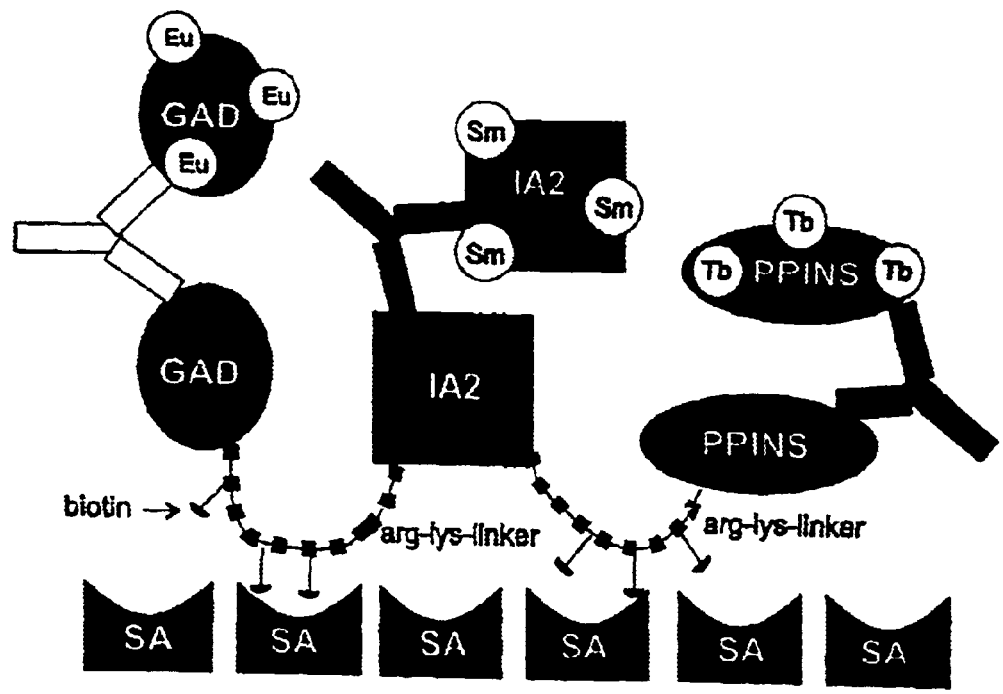
FIG. 4 shows the fusion protein according to this invention, attached to a solid support, autoantibodies attached to epitopes of said protein, and labeled reagents bound to said autoantibodies, wherein the reagents are labeled with different labels.

The term "epitope" can be an amino acid sequence anything from very few (about 5 to 10) amino acids of the autoantigens up to the whole autoantigen. Preferable lengths of the epitopes are represented by the underlined amino acid sequences in FIGS. 2a and 2b, and the whole antigen sequence is disclosed in FIG. 2c. Thus, the epitope of IA2 comprises preferably the amino acids 771–979 of the amino acid sequence shown in FIG. 2a. Another preferred alternative is the whole intracellular domain (amino acids ranging from about 576 to 979 of the sequence in FIG. 2a). The epitope of GAD65 comprises preferably the amino acids 102–585 of the amino acid sequence shown in FIG. 2b, and the epitope of PPINS comprises preferably all the amino acids 1–110 of the polypeptide shown in FIG. 2c. It should be noted that the above mentioned specific sequences are examples only.

According to a preferred embodiment, the fusion protein has epitopes of each of the autoantigens GAD65, IA2 and PPINS. Such a fusion protein allows simultaneous detection of autoantibodies specific for any of said autoantigens.

Said fusion protein containing epitopes of GAD65, IA2 and PPINS is formed by combining these domains via short peptides consisting of amino acid residues, e.g. lysine and arginine residues.

The epitopes from distinct autoantigens will be linked together via short peptides containing e.g. several lysine residues, which allows preferential labeling of these lys-residues. For construction of the polygenic cDNA, the linker-encoding cDNA contains a recognition site for a rarely cutting restriction enzyme such as Not I or Sgf I (see FIGS. 1a and 1b).

These linker residues may be connected to a member of an affinity binding pair so as to enable the binding of said fusion protein to a solid phase. The bioaffinity pair may be e.g. biotin—streptavidin. The residues (lysine) can be biotinylated after which the fusion protein is attached to a streptavidin-coated solid phase. The solid phase can e.g. be a well of a microtitration strip or plate. Alternatively, the solid phase consists of microparticles.

The fusion protein can alternatively be bound to the solid phase by direct adsorption. Furthermore, the fusion protein can be covalently linked to the solid phase. In this case the fusion protein must be provided with groups able to create a covalent bond with the solid phase. FIGS. 2 and 3 show the amino acid sequences and the nucleotide sequences, respectively, of the preferred epitopes.

The following illustrates the construction of the fusion protein and its preparation.

The N-terminus of the hybrid protein will contain a flag peptide NH2-DYKDDDDK-COOH (SEQ ID NO:1) with a free N-terminal amino group to allow recognition of the protein using M1 monoclonal antibody (ATCC cell line nr. HB 9259). This enables detection of the protein in SDS-PAGE where not all monoclonals function.

At the carboxy-terminal end of the fusion protein and in the single antigens a motif X-X-G-S-H-H-H-H-H-H (SEQ ID NO:11) is introduced to allow purification of the protein with metal chelate affinity chromatography and detection with monoclonal antibody against this epitope (Cedarlane Laboratories Ltd, Canada).

The GAD65 gene (Bu et al. 1992) is, for example, amplified with PCR (nucleotides 1311–1755) in such a manner that 101 amino acid residues are removed from the N-terminus.

The 3'-end oligonucleotide contains 17 bases complementary to the mRNA of GAD65 and an additional sequence encoding half of a peptide forming the bridge between GAD65 and IA2 domains.

The nucleotide sequence of the bridge is for example

Not I
GAD65-AAGAAGAA<u>GCGGCCGC</u>GAAAGAAGAAG-IA2 (SEQ ID NO:12; amino acid sequence of the peptide KKKRPRKKK (SEQ ID NO: 2)), or Sfg I
GAD65-AAGAAGAA<u>GCGATCGC</u>GAAAGAAGAAG-IA2 (SEQ ID NO:13; amino acid sequence KKKRSRKKK (SEQ ID NO:4)). The restriction enzyme recognition sites are underlined in the middle. The fragments are made from a plasmid harbouring said cDNAs with PCR and digested with appropriate restriction enzymes (e.g. Not I or Sfg I) and cloned into appropriate vectors. The GAD65 part is linked to IA2 and this to PPINS, using general cloning techniques.

The PPINS gene 5'-oligo contains half of the polylysine-arginine-encoding sequence with a Not I or Sfg I site for coupling to the IA2 gene 3'-end. The 3'-oligo of PPINS has a histidine hexapeptide-encoding sequence to enable antibody recognition and metal chelate chromatography purification and/or immobilization if necessary (Mauch et al. 1993).

Purified, restriction enzyme-treated PCR fragments are cloned in a FastBac derivative and *E.coli* DH10Bac cells are transfected with the plasmid. Recombinant clones are selected and DNA isolated and transfected into Sf9 insect cells.

Virus-producing cells are cultivated and stock virus made. Large-scale cultures are used to produce recombinant single proteins and the polyprotein.

SDS-PAGE/Western analysis is used to analyse size and immunoreactivity of the recombinant polyproteins. The proteins are blotted onto a nitrocellulose or nylon membrane and GAD/IA2/PPINS antibodies used to detect the product visualised with enhanced chemiluminescence, ECL.

For purification of the polyprotein GAD65-specific monoclonal antibody (GAD6, Developmental Studies Hybridoma Bank, Iowa University) is immobilized to Sepharose 4B activated with cyanogen bromide (Pharmacia, Uppsala, Sweden). Elution of the protein is performed at low pH (3–4) and solubility is achieved by adding detergents (e.g. Nonidet or Tween) to allow dissociation from the membranes.

The steps from cloning to large scale production can be described in more detail as follows:

1. Cloning into the pK503-9 vector (Kari Keinänen VTT Finland), a derivative of pFastBac (Gibco BRL Paisley Scotland) of GAD65, or IA2 or PPINS gene, each containing a flag recognition signal (FLAG®, Immunex Corporation) for antibody detection and a signal peptide for ecdysone glucotransferase (EGT) for transport into the endoplasmatic reticulum for removal of the signal peptide with simultaneous release of N-terminal aspartate for M1 antibody recognition. The constructs contain each a X-X-G-S-H-H-H-H-H-H carboxyterminal peptide (SEQ ID NO:11) to allow metal chelate affinity purification and detection with specific antibody (Cedarlane, Canada) of the product.
2. Transformation into competent *E. coli* DH10Bac cells of the plasmids containing the single genes.
3. Isolation of recombinant Bacmid DNA and transfection with the fused DNA of the Sf9 or Hi-5 insect cells.
4. Production of recombinant stock virus.
5. Large scale production of the proteins.
6. Cloning into pK503-9 vector of a cDNA construct for the fusion protein (FP) comprising GAD65 (nt 1311–1755; aa 102–585)-IA2(nt 2313–2937; aa 771–979)-PPINS (nt 2424–2610 and 3396–3539 (of the genomic DNA sequence, accession No. V00565); aa 1–110) in all alternative orders.
7. Transformation into competent *E. coli* DH10Bac cells of the plasmids containing the fusion protein.
8. Isolation of recombinant Bacmid DNA and transfection with the fused DNA of the Sf9 or Hi-5 insect cells.
9. Production of recombinant stock virus.
10. Large scale production of the fusion protein.

In case the baculovirus expression system does not work optimally, alternative systems such as *E.coli*, yeast, or in vitro transcription translation assay (Petersen et al. 1994) will be used for production of said polypeptides.

The present invention relates further to the use of the fusion protein in an immunoassay for the detection of several pancreatic beta-cell autoantibodies in IDDM patients and prediabetic sera. The assay may detect patients at risk of developing IDDM, i.e. having a pre-IDDM condition. As a multicomponent assay, the method could also be used to predict the time point of onset of the disease. The methodology which combines epitopes of several islet beta cell autoantigens increases the informativity and prediction value of the test aimed at prediction of risk and onset of disease in individuals genetically predisposed to IDDM.

Figure 5:
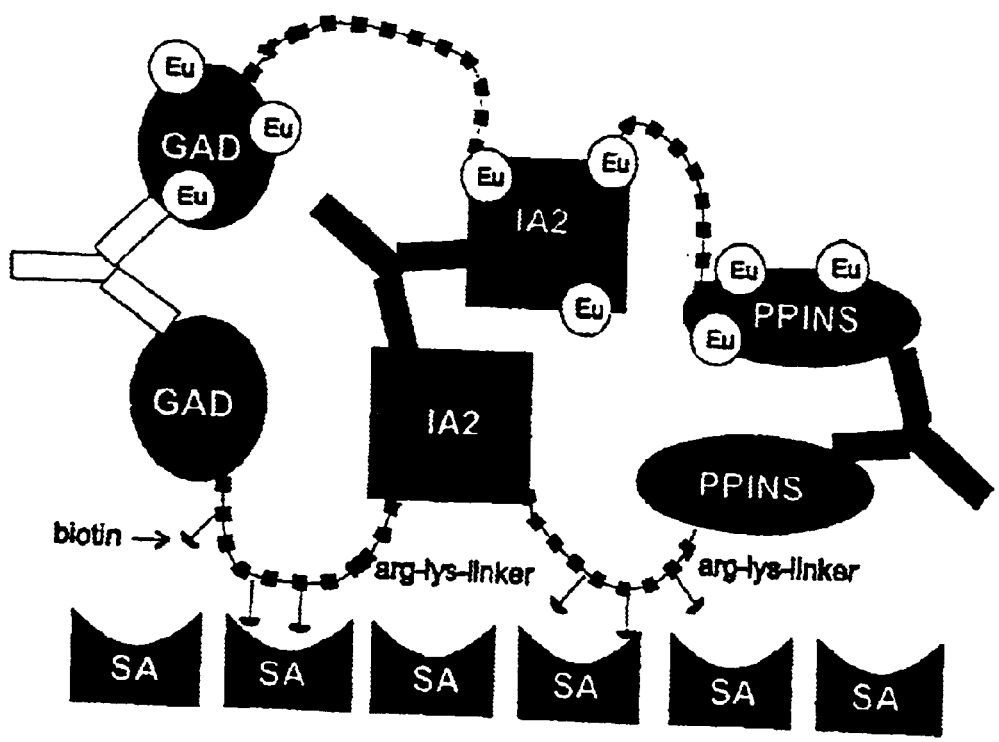
FIG. 5 shows the fusion protein according to this invention attached to a solid support, autoantibodies attached to epitopes of said protein, and labeled reagents bound to said autoantibodies, wherein the reagents are labeled with the same label.

In the immunoassay according to this invention, a sample of the person's body fluid (e.g. serum) is incubated with the fusion protein bound to a solid surface, e.g. a microtitration plate. The bound autoantigens are thereafter detected with a labeled reagent. The reagents can be the single autoantigens GAD65, IA2 and PPINS; or proteins comprising epitopes thereof. These reagents are used to detect free antigen-binding regions (V-regions) on the bound autoantibodies. One variant of the method will be used for differential detection of the individual autoantigen specificities of the antibody in one assay if individual autoantigens (AAGs) labeled with three different labels are used (see FIG. 4). Alternatively, when the polyprotein (the fusion protein) is labeled with only one label, it can be used to reveal the sum of these three reactivities in the sample (FIG. 5). The same result is achieved if the single antigens are all labeled with the same label. The labeled reagent can further be an anti-human monoclonal antibody. In this case the assay can reveal only the sum of the three autoantibodies.

The technique which involves use of the label attached to the fusion protein or individual autoantigens circumvents several problems encountered in the conventional assays. First, there is little or no nonspecific binding to the vials due to the fact that the carrier surfaces have already been blocked with the corresponding antigen. Second, the attachment via a bioaffinity pair such as streptavidin/biotin interaction to the vial and use of a flexible peptide between the individual antigenic epitopes enable free motion and folding of the protein in the solution (FIG. 5).

The label can be any suitable label. However, according to a preferred embodiment, the label is a lanthanide. In case three different labels are used, said labels can be e.g. Eu, Sm, Tb and Dy (Siitari et al. 1990; Hemmilä et al. 1993). In such a case the detection is based on time-resolved fluorescence.

The free labeled reagent can be removed after the incubation step before the signal is quantified (heterogeneous assay), or the signal can be quantified without foregoing removal of the free labelled reagent (homogeneous assay).

The procedures are preferably automatized. Automatization of the procedures involves laboratory robots which apply samples onto cover slips and the fluorescence is detected in an micro array system in an appropriate unit (Wallac OY, Finland).

The simultaneous detection of antibodies against the three autoantigens increases the capacity to process large sample series. The use of a micro array system substantially increases the capacity. This has become necessary as nation-wide screenings of newborns are undertaken in several research centers.

The test principle using time-resolved fluoroimmunoassay (TR-FIA) offers an extremely sensitive means for detection of autoantibodies with minimum amount of nonspecific reactivity due to used specific antigen label. The longevity of the lanthanide label is also an advantage as compared to radiolabel.

The system allows retaining of important conformational epitopes of the antigen as immobilization of the polyprotein is via specific flexible intervening sequences and causes minimal tortion to the antigen.

The following illustrates the use of the fusion protein in an immunoassay:

To the polyprotein (fusion protein) biotin is bound in limiting conditions to prevent other than the lysine residues of the linker peptide to be biotinylated. Streptavidine-coated microscope slides are treated with biotin—fusion protein and the residual sites are blocked with bovine serum albumin or another suitable binding protein.

M1 flag-specific monoclonal antibody will be used to monitor binding onto solid support of free recombinant autoantigens while autoantigen-specific monoclonals (e.g. GAD1, GAD6, MICA-3 (Boehringer) etc.) will be used to detect availability of specific epitopes. After incubation with sample sera, Eu-labeled GAD65, Sm-labeled IA2 and Tb-labeled PPINS (produced as a single protein with the baculosystem) are printed robotically onto the microscope slides in four quadrants covering an area of about 1 cm$^2$, allowed to bind, washed and dried in vacuum, and the fluorescence is measured on TR fluorometer.

The functionality of the method is tested using IDDM sera known to be positive for one or more of the antigens used.

For specificity testing recombinant GAD65, IA2 and PPINS, or fusion protein are added into patient sample to preadsorb specific antibodies.

The informativity will be compared with conventional systems. Statistical tests will be used to create best possible segregation of the positive and negative assay values.

The high density array system is fully automated.

The invention is further illustrated by the following examples.

EXAMPLE 1

Labeling Procedure

Isothiocyantophenyl-DTTA-Eu, or Tb, or Sm (Mukkala 1989) will be used for labeling of the FP or the single autoantigens. Mainly the protocols of Lövgren & Petterson (1990) and Hemmilä et al. (1984) will be followed. 30–100 fold molar excess of the label substance will be used giving approximately 10–12 lanthanide molecules per protein molecule. For Tb, 500 fold excess will be used. The coupling is carried out for 18 hr at 0° C. in 0.1 M bicarbonate buffer pH 9.2. The Eu (Tb,Sm)-AAg complex is separated from free Eu (Tb, Sm) by gel filtration in a Sepharose 6B column equilibrated with 0.05 M Tris-HCl buffer pH 7.75 containing 0.9% NaCl and 0.05% NaN$_3$. The Eu-AAg complex is stored at 4° C.

EXAMPLE 2

Immunoassay

The assay is performed in the wells of polystyrene microtitration strip coated with unlabeled autoantigen preparate for 18 hr at 25° C. in 0.1 M bicarbonate buffer pH 9.6 (Siitari & Kurppa 1987). The strips are washed prior to use with 0.9% NaCl containing 0.05% Tween 20 and 0.3% Germal II. To each well 100 µl of diluted (1:10) serum is added and incubated for 1 hr at 40° C., washed 2× with the wash solution and 200 µl of the Eu-labeled autoantigen fraction (50 ng/well) is added.

The strips are incubated for 1 hr at 40° C. The strips are washed 5× with the washing solution. Thereafter Enhancement Solution (EG&G Wallac) 200 µl/well is added. Strips are shaken for 10 min in a plate shaker and measured in EG&G Wallac Victor fluorometer for 1s/specimen. The photons emitted are measured as counts/s. Automated data reduction program calculates mean value of duplicates and the coefficient of variation (CV %).

For future development, the assay formate will be miniaturized e.g. by immobilizing the autoantigen molecules onto microparticles (Lövgren et al. 1997) or as a microarray onto glass cover slips.

It will be appreciated that the methods of the present invention can be incorporated in the form of a variety of embodiments, only a few of which are disclosed herein. It will be apparent for the specialist in the field that other embodiments exist and do not depart from the spirit of the invention. Thus, the described embodiments are illustrative and should not be construed as restrictive.

References

Atkinson M A, Kaufman D L, Newman D, Tobin A J, MacLaren N K. 1993. Islet cell cytoplasmic autoantibody reactivity to glutamate decarboxylase in insulin-dependent diabetes. J. Clin Invest. 91: 350–56.

Baekkeskov S, Nielsen, J H, Marner B, Blide T, Ludvigson J. Lenmark Å, 1982. Autoantibodies in newly diagnosed diabetic children immunoprecipitate human pancreatic islet cell proteins. Nature. 298:167–169.

Bell, G I, Pictet, R L, Rutter, W J, Cordell, B, Tischer, E and Goodman, H M 1980. Sequence of the human insulin gene. Nature. 284: 26–32.

Berg H, Walter M, Mauch L, Seissler J, Northemann W. 1993. Recombinant human preproinsulin. Expression, purification and reaction with insulin autoantibodies in sera from patients with insulin-dependent diabetes mellitus. J Immunol Methods. 164: 221–31.

Bingley P J, Christie M R, Bonifacio E, et al. 1994. Combined analysis of autoantibodies improves prediction of IDDM in islet cell antibody-positive relatives. Diabetes. 43: 1113–1120.

Bu D F, Erlander M G, Hitz B C, Tillakaratne N J, Kaufman D L, Wagner-McPherson C B, Evans G A, Tobin-A J. 1992. Two human glutamate decarboxylases, 65-kDa GAD and 67-kDa GAD, are each encoded by a single gene. Proc. Natl. Acad. Sci. U.S.A. 89: 2115–2119.

Falorni A, Ackefors M, Carlberg C, Daniels T, Persson B, Robertson J, Lernmark Å. 1996. Diagnostic sensitivity of immunodominant epitopes of glutamic acid decarboxylase (GAD65) autoantibodies in childhood IDDM. Diabetologia. 39: 1091–1098.

Fischer E H, Charbonnean H, Tonks N K. 1991. Protein tyrosine phosphatases: a diverse family of intracellular and transmembrane enzymes. Science. 253: 401–406.

Hemmilä I, Dakubu S, Mukkala V-M, Siitari H, Lövgren T. 1984. Europium as a label in time-resolved immunofluorimetric assays. Anal. Biochem. 137: 335–343.

Hemmilä I, Mukkala V-M, Latva M, Kiilholma P. 1993. Di- and tetracarboxylate derivatives of pyridines, bipyridines and terpyridines as luminogenic reagents for time-resolved fluorometric determination of terbium and dysprosium. Journal of Biochemical and Biophysical Methods. 26: 283–290.

Kim, J, M Namchuk, T Bugawan, Q Fu, M Jaffe, Y G Shi, H J Aanstoot, C W Turck, H Erlich, V Lennon, and S Baekkeskov. 1994. Higher autoantibody levels and recognition of a linear NH2-terminal epitope in the autoantigen GAD(65), distinguish Stiff-Man syndrome from insulin-dependent diabetes mellitus. Journal of Experimental Medicine. 180: 595–606.

Lampasona V, Bearzatto M, Genovese S, Bosi E, Ferrari M, Bonifacio E. 1996. Autoantibodies in insulin-dependent diabetes recognize distinct cytoplasmic domains of the protein tyrosine phosphatase-like IA-2 autoantigen. J. Immunol. 157: 2707–2711.

Lövgren, T, Heinonen, P, Lehtinen, P, Hakala, H, Heinola J, Harju J., Takalo, H., Mukkala, V-M, Schmiod, R, Lönnberg, H, Petterson, K and Iitiä, A 1997. Sensitive bioaffinity assays with individual microparticles and time-resolved fluorometry. Clin. Chem. 43: 1937–1943.

Lövgren T and Petterson K 1990. Time-resolved fluoroimmunoassay: advatages and limitations. In: CRC Luminescence immunoassays and molecular applications, Eds. van Dyke K, van Dyke R CRC Press Inc. Boca Raton, Fla., pp. 233–253.

Mauch, L Seissler, J, Haubruck, H, Cook, N J, Abney, C C, Berthold, H, Wirbelauer, C, Liedvogel, a, Scherbaum, W A and Northemann, W 1993. Baculovirus-mediated expression of human 65 kDa and 67 kDa glutamic acid decarboxylases in SF9 insect cells and their relevance in diagnosis of insulin-dependent diabetes mellitus. J. Biochem. Tokyo. 113: 699–704.

Mehta HB, Vold B S, Minkin S, Ullman E. 1996. DELISA: sensitive nonisotopic assay for GAD65 autoantibodies, a key risk-assessment marker for insulin-dependent diabetes mellitus. Clin. Chem. 42: 263–269.

Mukkala V-M, Mikola H, Hemmilä I. 1989. The synthesis and use of activated N-benzyl derivatives of diethylenetriaminetetraacetic acids: alternative reagents for labeling of antibodies with metal ions. Anal. Biochem. 176: 319–325.

Petersen, J S, Moody H A, Karlsen A E, et al. 1994. Detction of GAD65 antibodies in diabetes and other autoimmune diseases using a simple radioligand assay. Diabetes. 43: 459–467.

Rabin D U, Pleasic S M, Shapiro J A, Yoo-Warren H, Oles J, Hicks J M, Goldstein D E, Rae P M M. 1994. Islet cell antigen 512 is a diabetes-specific islet autoantigen related to protein tyrosine phosphatases. J. Immunol. 152: 3183–3188.

Sabbah, E, Kulmala P. Veijola R, Vahasalo P, Karjalainen J. Tuomilehto-Wolf E, Akerblom H K, and Knip M. 1996. Glutamic acid decarboxylase antibodies in relation to other autoantibodies and genetic risk markers in children with newly diagnosed insulin-dependent diabetes. J. Clin. Endocrinol. Metab. 81: 2455–2459.

Siitari & Kurppa 1987. Time-resolved fluoroimmunoassay in the detection of plant viruses. J. Gen. Virol. 68: 1423–1428.

Siitari, H, Turunen, P, Schrimsher, J & Nunn, H 1990. New sensitive and specific assay for human immunodeficiency virus antibodies using labeled recombinant fusion protein and time-resolved fluoroimmunoassay. J. Clin. Microbiol. 28: 2022–2029.

Snorgaard O, Kiens L L, Roder M E, Hartling S G, Dinesen B, Binder C. Proinsulin immunoreactivity inrecent-onset IDDM: the significance of insulin antibodies and insulin autoantibodies. Diabetes-Care. 19: 146–150.

Verge C F, Gianani R, Kawasaki E, Yu L, Pietropaolo M, Chase H P, and Eisenbarth G S. 1996, 379–383 and Verge C F, Howard N J, and Rowley M J et al. 1994. Combined analysis of autoantibodies improves prediction of IDDM in islet cell antibody-positive relatives. Diabetologia. 37: 1113–1120.

Zhang, Z J, Davidson L, Eisenbarth G, and Weiner H L. 1991. Suppression of Diabetes in Nonobese Diabetic Mice by Oral Administration of Porcine Insulin. Proc. Natl. Acad. Sci. U.S.A. 88: 10252–10256.

Zhang, B, Lan, M, and Notkins, A L 1997. Autoantibodies to IA-2 in IDDM: Location of major antigenic determinants. Diabetes. 46: 40–43.

---

What is claimed is:

1. A fusion protein presenting epitopes of at least two autoantigens wherein said autoantigens are selected from the group consisting of: preproinsulin (PPINS), glutamic acid decarboxylase (GAD65) and islet cell antigen (IA2), wherein said epitopes are connected with a linker peptide, wherein said linker peptide is selected from the group consisting of KKKRPRKKK (SEQ ID NO:2) and KKKRSRKKK (SEQ ID NO:4), said fusion protein being able to bind to a solid phase.

2. The fusion protein according to claim 1 having epitopes of each of the autoantigens GAD65, IA2 and PPINS.

3. The fusion protein according to claim 2 wherein
   the epitope of IA2 comprises the amino acids 771–979 of SEQ ID NO:5,
   the epitope of GAD65 comprises the amino acids 102–585 of SEQ ID NO:6, and
   the epitope of PPINS comprises all the amino acids 1–110 of SEQ ID NO:7.

4. The fusion protein according to claim 1, wherein said linker peptide is provided with a member of an affinity binding pair for facilitating the binding of said fusion protein to the solid phase.

5. The fusion protein according to claim 4 wherein the affinity binding pair is biotin-streptovidin.

6. A cDNA encoding the fusion protein according to claim 1 wherein said cDNA comprises nucleotide sequences encoding epitopes of at least two autoantigens wherein said autoantigens are selected from the group consisting of: preproinsulin (PPINS), glutamic acid decarboxylase (GAD65) and islet cell antigen (IA2).

7. A cDNA encoding the fusion protein according to claim 3 wherein said cDNA comprises the nucleotide sequences
   a) nucleotides 1311 to 1755 of SEQ ID NO:8 encoding GAD65, aa 102–585, b) nucleotides 2313 to 2937 of SEQ ID NO:9 encoding IA2, aa 771–979, and c) nucleotides 2424 to 2610 and 3397 to 3539 of SEQ ID NO:10 encoding PPINS, aa 1–110, where said nucleotide sequence a), b) and c) can appear in any relative order.

8. A vector comprising the cDNA according to claim 6.

9. An *E. coli* cell encompassing the cDNA according to claim 6.

10. A vector comprising the cDNA according to claim 7.

11. A fusion protein presenting epitopes of at least two autoantigens selected from the group consisting of glutamic acid decarboxylase (GAD65), islet cell antigen (IA2), and preproinsulin, wherein said fusion protein comprises a label and a linker peptide wherein said linker peptide is selected from the group consisting of KKKRPRKKK (SEQ ID NO:2) and KKKRSRKKK (SEQ ID NO:4).

12. The fusion protein of claim 11 wherein said label is a lanthanide.

13. The fusion protein of claim 1 wherein said linker peptide is labeled with a member of an affinity binding pair for facilitating binding of said fusion protein to said solid phase.

14. The fusion protein of claim 13 wherein said affinity binding pair is biotin-streptavidin.

15. The fusion protein of claim 11 wherein said linker peptide is labeled with a member of an affinity binding pair for facilitating binding of said fusion protein to said solid phase.

16. The fusion protein of claim 15 wherein said affinity binding pair is biotin-streptavidin.

* * * * *

UNITED STATES PATENT AND TRADEMARK OFFICE
CERTIFICATE OF CORRECTION

PATENT NO. : 6,770,460 B1
DATED : August 3, 2004
INVENTOR(S) : Hinkkanen

It is certified that error appears in the above-identified patent and that said Letters Patent is hereby corrected as shown below:

Title page,
Item [57], ABSTRACT, the word "wherenin" should read -- wherein --.

Column 32,
Lines 57, claim 5 should read as follows:
-- 5. The fusion protein according to claim 1, wherein said linker peptide is provided with a member of an affinity binding pair. --.

Column 34,
Line 3, claim 13 should read as follows:
-- 13, The fusion protein of claim 1 wherein said linker peptide is labeled with a member of an affinity binding pair. --.
Line 10, claim 15 should read as follows:
-- 15. The fusion protein of claim 11 wherein siad linker peptide is labeled with a member of an affinity binding pair. --.

Signed and Sealed this

Sixteenth Day of August, 2005

JON W. DUDAS
*Director of the United States Patent and Trademark Office*